(12) United States Patent
Hakonarson et al.

(10) Patent No.: US 10,704,098 B2
(45) Date of Patent: Jul. 7, 2020

(54) DIAGNOSIS AND TREATMENT OF GENETIC ALTERATIONS ASSOCIATED WITH EOSINOPHILIC ESOPHAGITIS

(71) Applicant: The Children's Hospital of Philadelphia, Philadelphia, PA (US)

(72) Inventors: Hakon Hakonarson, Malvern, PA (US); Patrick Sleiman, Philadelphia, PA (US)

(73) Assignee: The Children's Hospital of Philadelphia, Philadelphia, PA (US)

( * ) Notice: Subject to any disclaimer, the term of this patent is extended or adjusted under 35 U.S.C. 154(b) by 0 days.

(21) Appl. No.: 15/522,470

(22) PCT Filed: Oct. 29, 2015

(86) PCT No.: PCT/US2015/058097
§ 371 (c)(1),
(2) Date: Apr. 27, 2017

(87) PCT Pub. No.: WO2016/077078
PCT Pub. Date: May 19, 2016

(65) Prior Publication Data
US 2018/0127824 A1 May 10, 2018

Related U.S. Application Data

(60) Provisional application No. 62/072,294, filed on Oct. 29, 2014.

(51) Int. Cl.
*C12Q 1/6883* (2018.01)

(52) U.S. Cl.
CPC ..... *C12Q 1/6883* (2013.01); *C12Q 2600/156* (2013.01); *C12Q 2600/158* (2013.01)

(58) Field of Classification Search
None
See application file for complete search history.

(56) References Cited

U.S. PATENT DOCUMENTS

2015/0361499 A1* 12/2015 Walker ............... G01N 33/6893
424/94.1

FOREIGN PATENT DOCUMENTS

WO 2006083390 A2 8/2006

OTHER PUBLICATIONS

Promega. 1997 Biological Research Products Catalog. p. 78.*
GeneCard for ANKRD27 available via URL: <genecards.org/cgi-bin/carddisp.pl?gene=ANKRD27>, printed on Mar. 4, 2019.*
Johansson et al. Diabetes. Mar. 2006. 55:826-833.*
Li et al BMC Genetics. 2010. 11:47.*
Gagneux et al Molecular Phylogenetics and Evolution. 2001. 18: 2-13.*
Hattersley et al. The Lancet. 2005. 366: 1315-1323.*
Mummidi et al Journal of Biological Chemistry 2000 vol. 275 No. 25 pp. 18946-18961.*
Halushka et al Nature. Jul. 1999. 22: 239-247.*
Sherrill et al J Allergy Clin Immunol. 2010. 126(1): 160-165.*
Rothenberg et al Nature Genetics. 2010. 42(4): 289-291 and Supplementary Methods and Figures.*
NCBI dbSNP submission ss70784815 for rs3815700, available via URL: < ncbi.nlm.nih.gov/projects/SNP/snp_ss.cgi?subsnp_id=ss70784815> Apr. 20, 2007.*
NCBI dbSNP, ss237659255 submission for rs10410895, May 1, 2010, available via URL: < ncbi.nlm.nih.gov/projects/SNP/snp_ss.cgi?subsnp_id=ss237659255>.*
Anonymous: "Illumina Introduces HumanHap558 Genotyping BeadChip; New HumanHap BeadChips Expand Genomic Coverage with Industry-Leading Performance : Business Wire", Jun. 28, 2006 (Jun. 28, 2006), Retrieved from the Internet: :URL:https: //www.businesswire.com/news/home/20060328005364/en/Illumina-Introduces-HumanHap550-Genotyping-BeadChip-New-HumanHap [retrieved on Feb. 27, 2818].
Sleiman, Patrick M., et al. "GWAS identifies four novel eosinophilic esophagitis loci", Nature Communications, vol. 5. 19 Nov. 19, 2014, p. 5593.
Partial Supplementary European Search Report, dated Mar. 6, 2018, Application No. 15858376.5.
International Search Report/Written Opinion issued in the related PCT/US2015/58097, filed Oct. 29, 2015.
Rothenberg ME, et al. "Common variants at 5q22 associate with pediatric eosinophilic esophagitis." Nature genetics, Apr. 1, 2010, vol. 42, No. 4, pp. 289-291.
Kottyan, Leah C., et al. "Genome-wide association analysis of eosinophilic esophagitis provides insight into the tissue specificity of this allergic disease." Nature genetics, Jul. 13, 2014, vol. 46, No. 8, pp. 895-900.
Adler, Adam J., et al. "Infinium assay for large-scale SNP genotyping applications." Journal of visualized experiments: JoVE, Nov. 19, 2013, vol. 81:e50683.
NCBI publication "Reference SNP (refSNP) Cluster Report: rs167769" (Annotation Release 107, Mar. 13, 2015). Retrieved from the internet via url: <https://www.ncbi.nlm.nih.gov/projects/SNP/snp_ref.cgi?rs=167769>.

* cited by examiner

*Primary Examiner* — Carla J Myers
(74) *Attorney, Agent, or Firm* — Kathleen D. Rigaut; Howson & Howson LLP

(57) ABSTRACT

Compositions and methods for the treatment and diagnosis of eosinophilic esophagitis disclosed.

8 Claims, 11 Drawing Sheets

DIAGNOSIS AND TREATMENT OF GENETIC ALTERATIONS ASSOCIATED WITH EOSINOPHILIC ESOPHAGITIS

This application is a § 371 national phase entry of PCT/US2015/058097 filed Oct. 29, 2015, which claims priority to U.S. Provisional Application No. 62/072,294 filed Oct. 29, 2014, the entire contents of each being incorporated herein by reference as though set forth in full.

This invention was made with government support under Grant No. HG006830-02 awarded by the National Institutes of Health. The U.S. Government has certain rights in the invention.

FIELD OF THE INVENTION

This invention relates to the fields of allergic disorders and genome wide analysis studies which facilitate identification of genetic alterations associated with such disorders. More specifically, the invention provides a new panel of genetic markers associated with eosinophilic esophagitis and methods of use thereof in diagnosis and screening assays for the identification of efficacious therapeutic agents.

BACKGROUND OF THE INVENTION

Numerous publications and patent documents, including both published applications and issued patents, are cited throughout the specification in order to describe the state of the art to which this invention pertains. Each of these citations is incorporated herein by reference as though set forth in full.

Eosinophilic esophagitis (EoE) is an inflammatory disorder of the esophagus histologically characterized by accumulation of eosinophils in the esophageal epithelium. Clinical symptoms of EoE include dysphagia, failure to thrive, vomiting and epigastric or chest pain. A diagnosis of EoE is made following endoscopy and biopsy upon finding isolated eosinophils in the esophagus having ruled out gastroesophageal reflux. Multiple reports indicate a gender bias, with males predominantly affected. The rate of co-existing atopic disease in other organs is high, with up to 70% of subjects presenting with asthma or atopic dermatitis. EoE is considered a food allergy-related disorder based on the high rate of food allergen sensitization and a higher rate of food anaphylaxis in cases compared with the general population. Furthermore, the majority of EoE cases undergo disease remission following introduction of an elemental formula diet that lacks allergens. Experimental modeling of EoE in mice has demonstrated a key role for adaptive immunity and Th2-cell cytokines (especially IL-5 and IL-13) in the disease process and a strong connection between allergic sensitization and inflammation in the respiratory tract and skin. EoE is inherited as a complex trait suggesting it is caused by multiple genetic variations interacting with environmental influences. Clearly, a need exists in the art for improved methods for diagnosis and management of this disorder.

SUMMARY OF THE INVENTION

In accordance with the present invention, a method for detecting a propensity for developing eosinophilic esophagitis (EoE) in a subject in need thereof is provided. An exemplary method comprises detecting the presence of at least one genetic alteration in a target gene identified in said subject wherein if said genetic alteration is present, said patient has an increased risk for developing eosinophilic esophagitis, wherein said genetic alteration is present in a gene sequence from one or more loci of c11orf30, STAT6, ANKRD27 and/or CAPN14 The present inventors have discovered that such loci comprise single nucleotide polymorphisms (SNP) that indicate that the genetic alteration is present. In certain embodiments, the step of detecting the presence of said SNP comprises performing a process selected from the group consisting of detection of specific hybridization, measurement of allele size, restriction fragment length polymorphism analysis, allele-specific hybridization analysis, single base primer extension reaction, and sequencing of an amplified polynucleotide. Kits for practicing the method described above are also within the scope of the invention.

In another aspect, the invention provides a method for identifying agents which modulate the development or progression of eosinophilic esophagitis. An exemplary method entails providing cells expressing at least one nucleic acid comprising a genetic alteration associated with EoE as described above, providing cells which express the cognate wild type sequence lacking the genetic alterations, contacting each cell type with a test agent and analyzing whether the agent alters a cellular parameter associated with the presence of eosinophilic esophagitis in the cells of step a) relative to those of step b), thereby identifying agents which alter said parameter. Such parameters include without limitation, increased expression of IL-5 or IL-13, epidermis development, epithelial cell differentiation, serine protease inhibition, altered cell cycle progression, or division, microtubule disruption, histone acetylation, DNA methylation, chromosomal segregation, ubiquitin conjugation, and phosphoinositide mediated signaling, and altered mitosis.

In particularly preferred embodiments, the agent alters mRNA or protein levels of the EoE associated genes of the invention, i.e., c11orf30, STAT6, ANKRD27 and CAPN14. Preferably, the alterations in expression levels are observed in blood or esophageal cells. Also provided are kits for practicing the screening method described above.

BRIEF DESCRIPTION OF THE DRAWINGS

FIG. 1A: Manhattan plot of the EoE discovery GWAS (n=603 cases and 3637 controls) −log 10 Pvals on the y-axis plotted against ascending physical position on the x-axis. The dotted red line represents the genome-wide significance threshold Pval≥5×10$^{-8}$. FIG. 1B: QQ plots of the EoE discovery GWAS (λ1.07), FIG. 1C replication GWAS (λ1.04), FIG. 1D. and meta-analysis (λ1.001).

FIG. 3A: SNPs in LD with rs55646091 and FIG. 3B: SNPs in LD with rs11236791.

DETAILED DESCRIPTION OF THE INVENTION

Figure 1A:
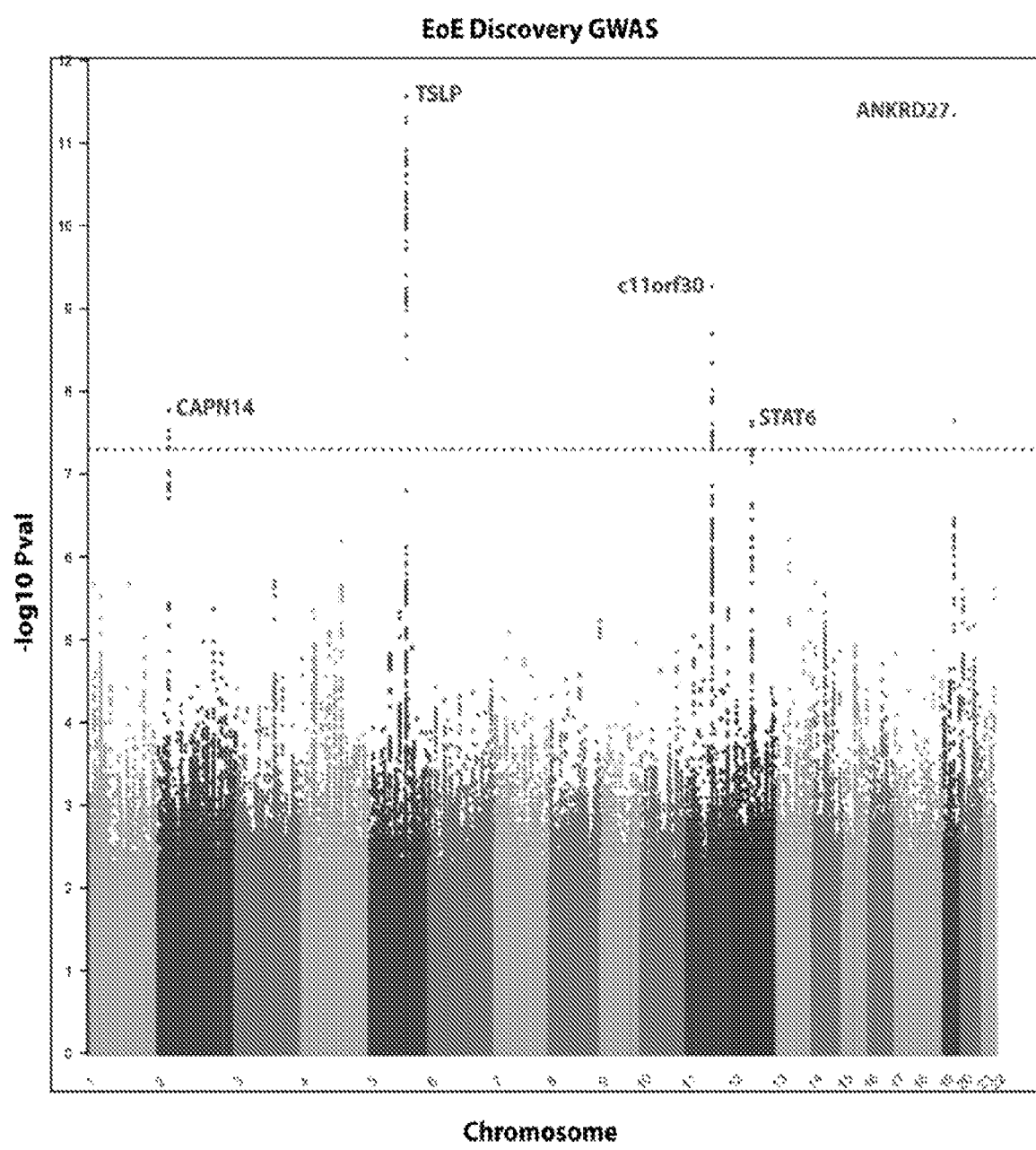
FIGS. 1A-1C.
Figure 1B:
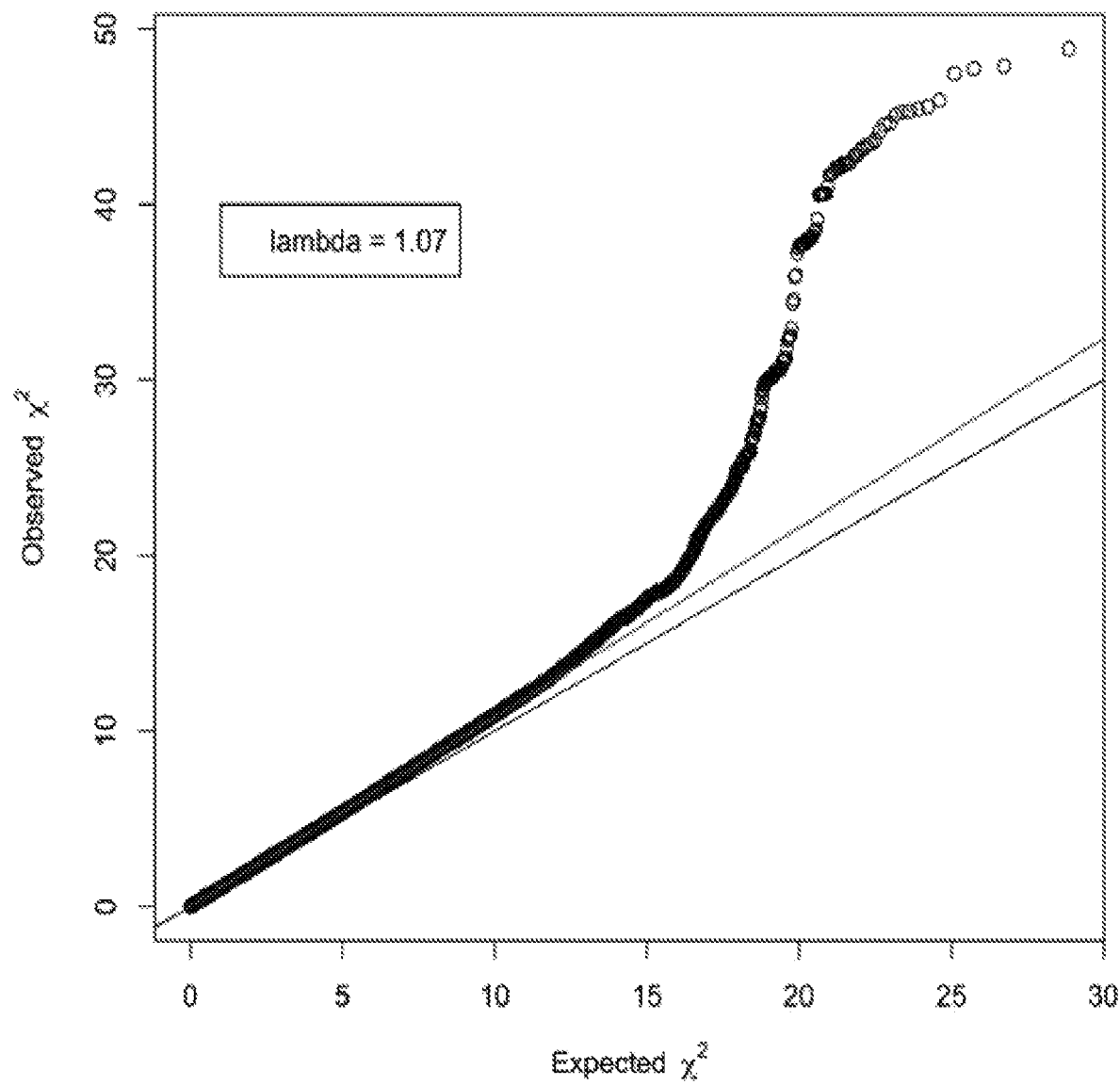
Figure 1C:
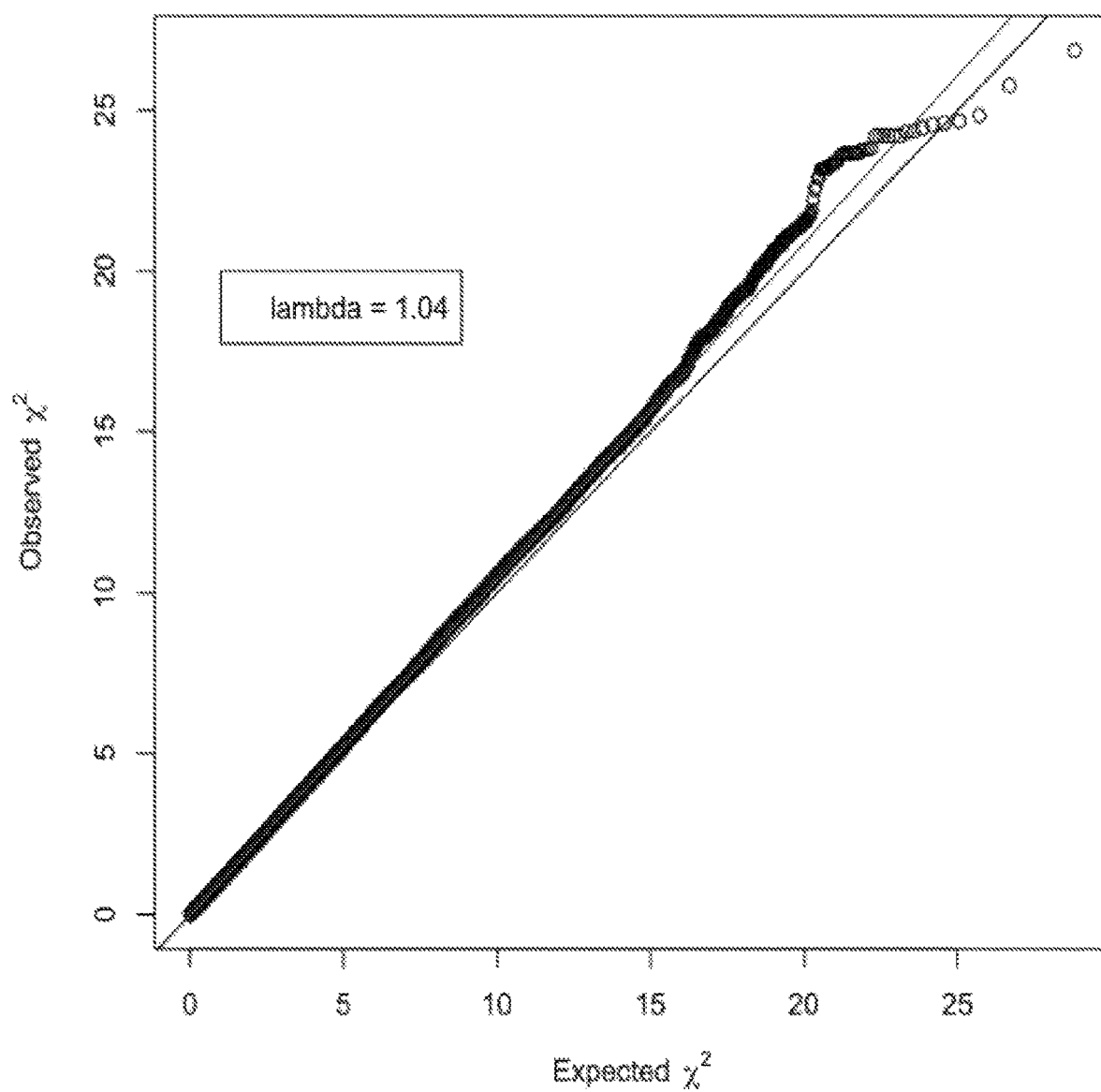
Figure 1D:
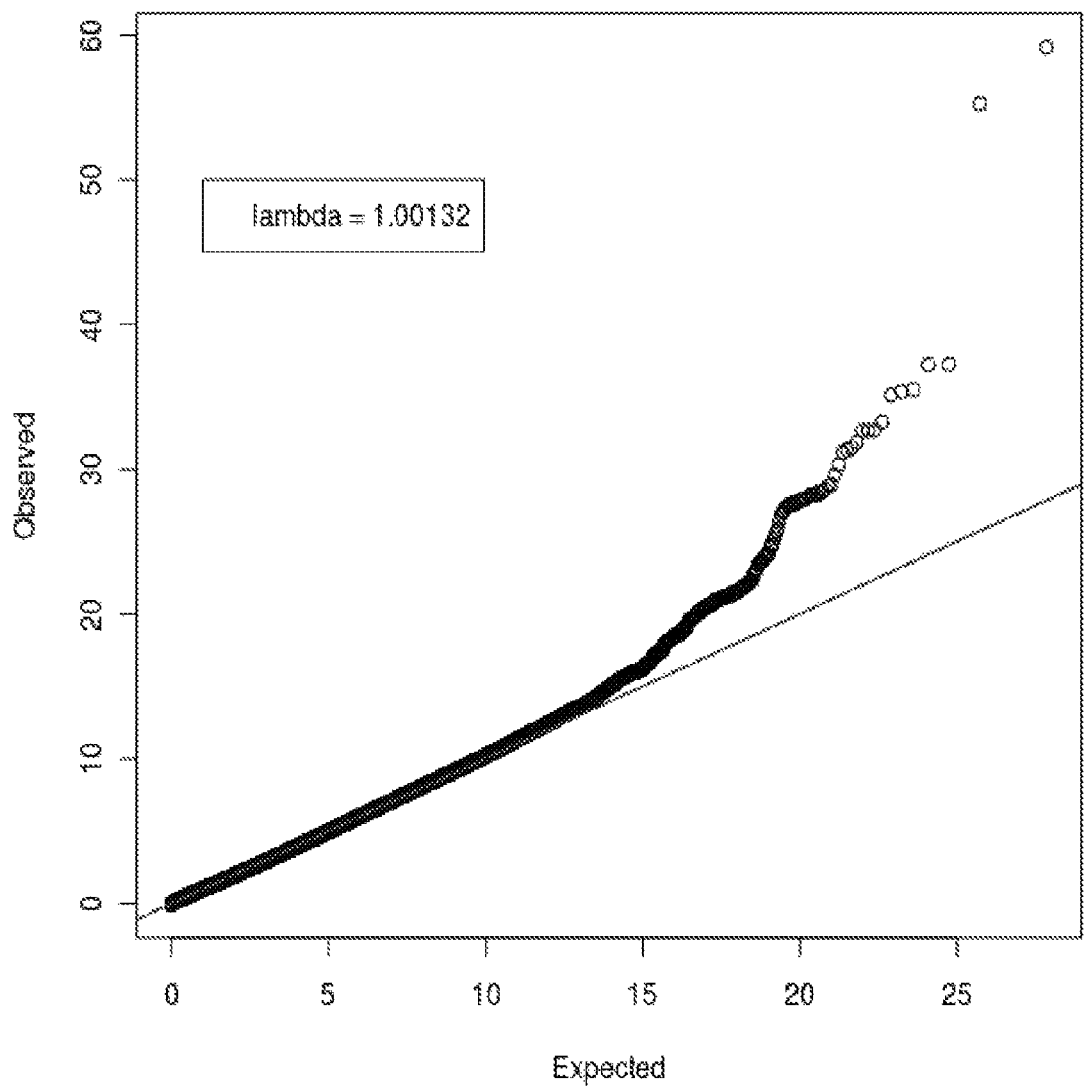

Eosinophilic esophagitis (EoE) is an allergic disorder characterized by infiltration of the esophagus with eosinophils. We had previously reported association of the TSLPI-WDR36 locus with EoE. Here, we report the association of four novel loci; c11orf30 and STAT6, which have been previously associated with both atopic and autoimmune disease, and two EoE-specific loci, ANKRD27 that regulates the trafficking of melanogenic enzymes to epidermal melanocytes and CAPN14, that encodes a calpain whose expression is highly enriched in the esophagus.

The following definitions are provided to facilitate an understanding of the present invention.

I. Definitions

For purposes of the present invention, "a" or "an" entity refers to one or more of that entity; for example, "a cDNA" refers to one or more cDNA or at least one cDNA. As such, the terms "a" or "an," "one or more" and "at least one" can be used interchangeably herein. It is also noted that the terms "comprising," "including," and "having" can be used interchangeably. Furthermore, a compound "selected from the group consisting of" refers to one or more of the compounds in the list that follows, including mixtures (i.e. combinations) of two or more of the compounds. According to the present invention, an isolated, or biologically pure molecule is a compound that has been removed from its natural milieu. As such, "isolated" and "biologically pure" do not necessarily reflect the extent to which the compound has been purified. An isolated compound of the present invention can be obtained from its natural source, can be produced using laboratory synthetic techniques or can be produced by any such chemical synthetic route.

The term "genetic alteration" as used herein refers to a change from the wild-type or reference sequence of one or more nucleic acid molecules. Genetic alterations include without limitation, base pair substitutions, additions and deletions of at least one nucleotide from a nucleic acid molecule of known sequence.

A "single nucleotide polymorphism (SNP)" refers to a change in which a single base in the DNA differs from the usual base at that position. These single base changes are called SNPs or "snips." Millions of SNP's have been cataloged in the human genome. Some SNPs such as that which causes sickle cell are responsible for disease. Other SNPs are normal variations in the genome.

A "copy number variation (CNV)" refers to the number of copies of a particular gene or segment thereof in the genome of an individual. CNVs represent a major genetic component of human phenotypic diversity. Susceptibility to genetic disorders is known to be associated not only with single nucleotide polymorphisms (SNP), but also with structural and other genetic variations, including CNVs. A CNV represents a copy number change involving a DNA fragment that is ~1 kilobases (kb) or larger (Feuk et al. 2006a). CNVs described herein do not include those variants that arise from the insertion/deletion of transposable elements (e.g., ~6-kb KpnI repeats) to minimize the complexity of future CNV analyses. The term CNV therefore encompasses previously introduced terms such as large-scale copy number variants (LCVs; Iafrate et al. 2004), copy number polymorphisms (CNPs; Sebat et al. 2004), and intermediate-sized variants (ISVs; Tuzun et al. 2005), but not retroposon insertions. The terminology "duplication-containing CNV" is also used herein below consistent with the CNV definition provided.

"EoE-associated SNP" or "EoE-associated specific marker" or EoE-associated informational sequence molecule" is a SNP or marker sequence which is associated with an altered risk of developing EoE not found normal in patients who do not have this disease. Such markers may include but are not limited to nucleic acids, proteins encoded thereby, or other small molecules. Thus, the phrase "EoE-associated SNP containing nucleic acid" is encompassed by the above description.

The term "solid matrix" as used herein refers to any format, such as beads, microparticles, a microarray, the surface of a microtitration well or a test tube, a dipstick or a filter. The material of the matrix may be polystyrene, cellulose, latex, nitrocellulose, nylon, polyacrylamide, dextran or agarose. EoE associated nucleic acids may be affixed or immobilized to a solid matrix. Affixed or immobilized as used herein refers to a linkage that is stable in solution, such that the nucleic acids remain attached to the solid matrix under different processing or experimental conditions.

The phrase "consisting essentially of" when referring to a particular nucleotide or amino acid means a sequence having the properties of a given SEQ ID NO. For example, when used in reference to an amino acid sequence, the phrase includes the sequence per se and molecular modifications that would not affect the functional and novel characteristics of the sequence.

The phrase "partial informative CNV" is used herein to refer to a nucleic acid that hybridizes to sequences comprising a duplication on a chromosome however, the partial informative CNV may not be identical to the duplication, rather, the CNV may correspond to only a portion of the duplication, but yet is still informative for the same.

"Target nucleic acid" as used herein refers to a previously defined region of a nucleic acid present in a complex nucleic acid mixture wherein the defined wild-type region contains at least one known nucleotide variation which may or may not be associated with EoE but is informative of the risk of EOE. The nucleic acid molecule may be isolated from a natural source by cDNA cloning or subtractive hybridization or synthesized manually. The nucleic acid molecule may be synthesized manually by the triester synthetic method or by using an automated DNA synthesizer. When cloning a target nucleic acid comprising a deletion, the skilled artisan is well aware of methods for selecting nucleic acids of a sufficient length flanking the affected region to facilitate cloning the region in to a vector of choice.

With regard to nucleic acids used in the invention, the term "isolated nucleic acid" is sometimes employed. This term, when applied to DNA, refers to a DNA molecule that is separated from sequences with which it is immediately contiguous (in the 5' and 3' directions) in the naturally occurring genome of the organism from which it was derived. For example, the "isolated nucleic acid" may comprise a DNA molecule inserted into a vector, such as a plasmid or virus vector, or integrated into the genomic DNA of a prokaryote or eukaryote. An "isolated nucleic acid molecule" may also comprise a cDNA molecule. An isolated nucleic acid molecule inserted into a vector is also sometimes referred to herein as a recombinant nucleic acid molecule.

With respect to RNA molecules, the term "isolated nucleic acid" primarily refers to an RNA molecule encoded by an isolated DNA molecule as defined above. Alternatively, the term may refer to an RNA molecule that has been sufficiently separated from RNA molecules with which it would be associated in its natural state (i.e., in cells or tissues), such that it exists in a "substantially pure" form.

By the use of the term "enriched" in reference to nucleic acid it is meant that the specific DNA or RNA sequence constitutes a significantly higher fraction (2-5 fold) of the total DNA or RNA present in the cells or solution of interest than in normal cells or in the cells from which the sequence was taken. This could be caused by a person by preferential reduction in the amount of other DNA or RNA present, or by a preferential increase in the amount of the specific DNA or RNA sequence, or by a combination of the two. However, it should be noted that "enriched" does not imply that there are no other DNA or RNA sequences present, just that the relative amount of the sequence of interest has been significantly increased.

It is also advantageous for some purposes that a nucleotide sequence be in purified form. The term "purified" in reference to nucleic acid does not require absolute purity (such as a homogeneous preparation); instead, it represents an indication that the sequence is relatively purer than in the natural environment (compared to the natural level, this level should be at least 2-5 fold greater, e.g., in terms of mg/ml). Individual clones isolated from a cDNA library may be purified to electrophoretic homogeneity. The claimed DNA molecules obtained from these clones can be obtained directly from total DNA or from total RNA. The cDNA clones are not naturally occurring, but rather are preferably obtained via manipulation of a partially purified naturally occurring substance (messenger RNA). The construction of a cDNA library from mRNA involves the creation of a synthetic substance (cDNA) and pure individual cDNA clones can be isolated from the synthetic library by clonal selection of the cells carrying the cDNA library. Thus, the process which includes the construction of a cDNA library from mRNA and isolation of distinct cDNA clones yields an approximately $10^{-6}$-fold purification of the native message. Thus, purification of at least one order of magnitude, preferably two or three orders, and more preferably four or five orders of magnitude is expressly contemplated. Thus the term "substantially pure" refers to a preparation comprising at least 50-60% by weight the compound of interest (e.g., nucleic acid, oligonucleotide, etc.). More preferably, the preparation comprises at least 75% by weight, and most preferably 90-99% by weight, the compound of interest. Purity is measured by methods appropriate for the compound of interest.

The term "complementary" describes two nucleotides that can form multiple favorable interactions with one another. For example, adenine is complementary to thymine as they can form two hydrogen bonds. Similarly, guanine and cytosine are complementary since they can form three hydrogen bonds. Thus if a nucleic acid sequence contains the following sequence of bases, thymine, adenine, guanine and cytosine, a "complement" of this nucleic acid molecule would be a molecule containing adenine in the place of thymine, thymine in the place of adenine, cytosine in the place of guanine, and guanine in the place of cytosine. Because the complement can contain a nucleic acid sequence that forms optimal interactions with the parent nucleic acid molecule, such a complement can bind with high affinity to its parent molecule.

With respect to single stranded nucleic acids, particularly oligonucleotides, the term "specifically hybridizing" refers to the association between two single-stranded nucleotide molecules of sufficiently complementary sequence to permit such hybridization under pre-determined conditions generally used in the art (sometimes termed "substantially complementary"). In particular, the term refers to hybridization of an oligonucleotide with a substantially complementary sequence contained within a single-stranded DNA or RNA molecule of the invention, to the substantial exclusion of hybridization of the oligonucleotide with single-stranded nucleic acids of non-complementary sequence. For example, specific hybridization can refer to a sequence which hybridizes to any EoE specific marker gene or nucleic acid, but does not hybridize to other nucleotides. Also polynucleotide which "specifically hybridizes" may hybridize only to an EOE-specific marker shown in the Tables contained herein. Appropriate conditions enabling specific hybridization of single stranded nucleic acid molecules of varying complementarity are well known in the art.

For instance, one common formula for calculating the stringency conditions required to achieve hybridization between nucleic acid molecules of a specified sequence homology is set forth below (Sambrook et al., Molecular Cloning, Cold Spring Harbor Laboratory (1989):

$$T_m = 81.5"C + 16.6 \text{ Log } [Na+] + 0.41(\% \ G+C) - 0.63(\% \text{ formamide}) - 600/\#bp \text{ in duplex}$$

As an illustration of the above formula, using [Na+]=[0.368] and 50% formamide, with GC content of 42% and an average probe size of 200 bases, the $T_m$ is 57"C. The $T_m$ of a DNA duplex decreases by 1-1.5"C with every 1% decrease in homology. Thus, targets with greater than about 75% sequence identity would be observed using a hybridization temperature of 42"C.

The stringency of the hybridization and wash depend primarily on the salt concentration and temperature of the solutions. In general, to maximize the rate of annealing of the probe with its target, the hybridization is usually carried out at salt and temperature conditions that are 20-25° C. below the calculated $T_m$ of the hybrid. Wash conditions should be as stringent as possible for the degree of identity of the probe for the target. In general, wash conditions are selected to be approximately 12-20° C. below the $T_m$ of the hybrid. In regards to the nucleic acids of the current invention, a moderate stringency hybridization is defined as hybridization in 6×SSC, 5×Denhardt's solution, 0.5% SDS and 100 µg/ml denatured salmon sperm DNA at 42° C., and washed in 2×SSC and 0.5% SDS at 55° C. for 15 minutes. A high stringency hybridization is defined as hybridization in 6×SSC, 5×Denhardt's solution, 0.5% SDS and 100 µg/ml denatured salmon sperm DNA at 42° C., and washed in 1×SSC and 0.5% SDS at 65° C. for 15 minutes. A very high stringency hybridization is defined as hybridization in 6×SSC, 5×Denhardt's solution, 0.5% SDS and 100 µg/ml denatured salmon sperm DNA at 42° C., and washed in 0.1×SSC and 0.5% SDS at 65° C. for 15 minutes.

The term "oligonucleotide," as used herein is defined as a nucleic acid molecule comprised of two or more ribo- or deoxyribonucleotides, preferably more than three. The exact size of the oligonucleotide will depend on various factors and on the particular application and use of the oligonucleotide. Oligonucleotides, which include probes and primers, can be any length from 3 nucleotides to the full length of the nucleic acid molecule, and explicitly include every possible number of contiguous nucleic acids from 3 through the full length of the polynucleotide. Preferably, oligonucleotides are at least about 10 nucleotides in length, more preferably at least 15 nucleotides in length, more preferably at least about 20 nucleotides in length.

The term "probe" as used herein refers to an oligonucleotide, polynucleotide or nucleic acid, either RNA or DNA, whether occurring naturally as in a purified restriction enzyme digest or produced synthetically, which is capable of annealing with or specifically hybridizing to a nucleic acid with sequences complementary to the probe. A probe may be either single-stranded or double-stranded. The exact length of the probe will depend upon many factors, including temperature, source of probe and use of the method. For example, for diagnostic applications, depending on the complexity of the target sequence, the oligonucleotide probe typically contains 15-25 or more nucleotides, although it may contain fewer nucleotides. The probes herein are selected to be complementary to different strands of a particular target nucleic acid sequence. This means that the probes must be sufficiently complementary so as to be able to "specifically hybridize" or anneal with their respective target strands under a set of pre-determined conditions. Therefore, the probe sequence need not reflect the exact complementary sequence of the target. For example, a non-complementary nucleotide fragment may be attached to the 5' or 3' end of the probe, with the remainder of the probe sequence being complementary to the target strand. Alternatively, non-complementary bases or longer sequences can be interspersed into the probe, provided that the probe sequence has sufficient complementarity with the sequence of the target nucleic acid to anneal therewith specifically.

The term "primer" as used herein refers to an oligonucleotide, either RNA or DNA, either single-stranded or double-stranded, either derived from a biological system, generated by restriction enzyme digestion, or produced synthetically which, when placed in the proper environment, is able to functionally act as an initiator of template-dependent nucleic acid synthesis. When presented with an appropriate nucleic acid template, suitable nucleoside triphosphate precursors of nucleic acids, a polymerase enzyme, suitable cofactors and conditions such as a suitable temperature and pH, the primer may be extended at its 3' terminus by the addition of nucleotides by the action of a polymerase or similar activity to yield a primer extension product. The primer may vary in length depending on the particular conditions and requirement of the application. For example, in diagnostic applications, the oligonucleotide primer is typically 15-25 or more nucleotides in length. The primer must be of sufficient complementarity to the desired template to prime the synthesis of the desired extension product, that is, to be able anneal with the desired template strand in a manner sufficient to provide the 3' hydroxyl moiety of the primer in appropriate juxtaposition for use in the initiation of synthesis by a polymerase or similar enzyme. It is not required that the primer sequence represent an exact complement of the desired template. For example, a non-complementary nucleotide sequence may be attached to the 5' end of an otherwise complementary primer. Alternatively, non-complementary bases may be interspersed within the oligonucleotide primer sequence, provided that the primer sequence has sufficient complementarity with the sequence of the desired template strand to functionally provide a template-primer complex for the synthesis of the extension product.

Polymerase chain reaction (PCR) has been described in U.S. Pat. Nos. 4,683,195, 4,800,195, and 4,965,188, the entire disclosures of which are incorporated by reference herein.

The term "vector" relates to a single or double stranded circular nucleic acid molecule that can be infected, transfected or transformed into cells and replicate independently or within the host cell genome. A circular double stranded nucleic acid molecule can be cut and thereby linearized upon treatment with restriction enzymes. An assortment of vectors, restriction enzymes, and the knowledge of the nucleotide sequences that are targeted by restriction enzymes are readily available to those skilled in the art, and include any replicon, such as a plasmid, cosmid, bacmid, phage or virus, to which another genetic sequence or element (either DNA or RNA) may be attached so as to bring about the replication of the attached sequence or element. A nucleic acid molecule of the invention can be inserted into a vector by cutting the vector with restriction enzymes and ligating the two pieces together. Vectors engineered to express nucleic acids encoding proteins having deletions can be generated by providing altered sequence along with flanking sequences of a sufficient length such that cloning into a vector is possible. Such flanking sequences can be between 10, 20, 50, 100, or 200 nucleotides in length.

Many techniques are available to those skilled in the art to facilitate transformation, transfection, or transduction of the expression construct into a prokaryotic or eukaryotic organism. The terms "transformation", "transfection", and "transduction" refer to methods of inserting a nucleic acid and/or expression construct into a cell or host organism. These methods involve a variety of techniques, such as treating the cells with high concentrations of salt, an electric field, or detergent, to render the host cell outer membrane or wall permeable to nucleic acid molecules of interest, microinjection, PEG-fusion, and the like.

The term "promoter element" describes a nucleotide sequence that is incorporated into a vector that, once inside an appropriate cell, can facilitate transcription factor and/or polymerase binding and subsequent transcription of portions of the vector DNA into mRNA. In one embodiment, the promoter element of the present invention precedes the 5' end of the EOE specific marker nucleic acid molecule such that the latter is transcribed into mRNA. Host cell machinery then translates mRNA into a polypeptide.

Those skilled in the art will recognize that a nucleic acid vector can contain nucleic acid elements other than the promoter element and the EOE specific marker nucleic acid molecule. These other nucleic acid elements include, but are not limited to, origins of replication, ribosomal binding sites, nucleic acid sequences encoding drug resistance enzymes or amino acid metabolic enzymes, and nucleic acid sequences encoding secretion signals, localization signals, or signals useful for polypeptide purification.

A "replicon" is any genetic element, for example, a plasmid, cosmid, bacmid, plastid, phage or virus, that is capable of replication largely under its own control. A replicon may be either RNA or DNA and may be single or double stranded.

An "expression operon" refers to a nucleic acid segment that may possess transcriptional and translational control sequences, such as promoters, enhancers, translational start signals (e.g., ATG or AUG codons), polyadenylation signals, terminators, and the like, and which facilitate the expression of a polypeptide coding sequence in a host cell or organism.

As used herein, the terms "reporter," "reporter system", "reporter gene," or "reporter gene product" shall mean an operative genetic system in which a nucleic acid comprises a gene that encodes a product that when expressed produces a reporter signal that is a readily measurable, e.g., by biological assay, immunoassay, radio immunoassay, or by colorimetric, fluorogenic, chemiluminescent or other methods. The nucleic acid may be either RNA or DNA, linear or circular, single or double stranded, antisense or sense polarity, and is operatively linked to the necessary control elements for the expression of the reporter gene product. The required control elements will vary according to the nature of the reporter system and whether the reporter gene is in the form of DNA or RNA, but may include, but not be limited to, such elements as promoters, enhancers, translational control sequences, poly A addition signals, transcriptional termination signals and the like.

The introduced nucleic acid may or may not be integrated (covalently linked) into nucleic acid of the recipient cell or organism. In bacterial, yeast, plant and mammalian cells, for example, the introduced nucleic acid may be maintained as an episomal element or independent replicon such as a plasmid. Alternatively, the introduced nucleic acid may become integrated into the nucleic acid of the recipient cell or organism and be stably maintained in that cell or organism and further passed on or inherited to progeny cells or organisms of the recipient cell or organism. Finally, the introduced nucleic acid may exist in the recipient cell or host organism only transiently.

The term "selectable marker gene" refers to a gene that when expressed confers a selectable phenotype, such as antibiotic resistance, on a transformed cell.

The term "operably linked" means that the regulatory sequences necessary for expression of the coding sequence are placed in the DNA molecule in the appropriate positions relative to the coding sequence so as to effect expression of the coding sequence. This same definition is sometimes applied to the arrangement of transcription units and other transcription control elements (e.g. enhancers) in an expression vector.

The terms "recombinant organism", or "transgenic organism" refer to organisms which have a new combination of genes or nucleic acid molecules. A new combination of genes or nucleic acid molecules can be introduced into an organism using a wide array of nucleic acid manipulation techniques available to those skilled in the art. The term "organism" relates to any living being comprised of a least one cell. An organism can be as simple as one eukaryotic cell or as complex as a mammal. Therefore, the phrase "a recombinant organism" encompasses a recombinant cell, as well as eukaryotic and prokaryotic organism.

The term "isolated protein" or "isolated and purified protein" is sometimes used herein. This term refers primarily to a protein produced by expression of an isolated nucleic acid molecule of the invention. Alternatively, this term may refer to a protein that has been sufficiently separated from other proteins with which it would naturally be associated, so as to exist in "substantially pure" form. "Isolated" is not meant to exclude artificial or synthetic mixtures with other compounds or materials, or the presence of impurities that do not interfere with the fundamental activity, and that may be present, for example, due to incomplete purification, addition of stabilizers, or compounding into, for example, immunogenic preparations or pharmaceutically acceptable preparations.

A "specific binding pair" comprises a specific binding member (sbm) and a binding partner (bp) which have a particular specificity for each other and which in normal conditions bind to each other in preference to other molecules. Examples of specific binding pairs are antigens and antibodies, ligands and receptors and complementary nucleotide sequences. The skilled person is aware of many other examples. Further, the term "specific binding pair" is also applicable where either or both of the specific binding member and the binding partner comprise a part of a large molecule. In embodiments in which the specific binding pair comprises nucleic acid sequences, they will be of a length to hybridize to each other under conditions of the assay, preferably greater than 10 nucleotides long, more preferably greater than 15 or 20 nucleotides long.

"Sample" or "patient sample" or "biological sample" generally refers to a sample which may be tested for a particular molecule, preferably an EoE specific marker molecule, such as a marker described hereinbelow. Samples may include but are not limited to cells, body fluids, including blood, serum, plasma, cerebral spinal fluid, urine, saliva, tears, pleural fluid and the like.

The terms "agent" and "compound" are used interchangeably herein and denote a chemical compound, a mixture of chemical compounds, a biological macromolecule, or an extract made from biological materials such as bacteria, plants, fungi, or animal (particularly mammalian) cells or tissues. Biological macromolecules include siRNA, shRNA, antisense oligonucleotides, peptides, peptide/DNA complexes, and any nucleic acid based molecule which exhibits the capacity to modulate the activity of the CNV or SNP-containing nucleic acids described herein or their encoded proteins. Agents and compounds may also be referred to as "test agents" or "test compounds" which are evaluated for potential biological activity by inclusion in screening assays described herein below.

The term "modulate" as used herein refers to increasing/promoting or decreasing/inhibiting a particular cellular, biological or signaling function associated with the normal activities of the genetic alteration containing molecules described herein or the proteins encoded thereby. For example, the term modulate refers to the ability of a test compound or test agent to interfere with signaling or activity of a gene or protein of the present invention.

II. Methods of Using EoE-Associated SNPs for Diagnosing a Propensity for the Development of EoE The present invention provides methods of diagnosing EoE in a patient or methods for identifying a patient having an increased risk of developing EoE. Diagnosis, as used herein, includes not only the initial identification of EoE associated with the genetic alterations described herein in a patient but confirmatory testing, or screening in patients who have previously been identified as having or likely to have EoE. The methods include the steps of providing a biological sample from the patient, measuring the amount of particular sets, or any or all of the EoE associated markers present in the biological sample, preferably a tissue and/or blood plasma sample, and determining if the patient has a greater likelihood of EoE based on the amount and/or type of EoE marker expression level determined relative to those expression levels identified in patient cohorts of known outcome. A patient has a greater likelihood of having EoE when the sample has a marker expression profile associated with patients previously diagnosed with EoE. The compositions and methods of the invention are useful for the prognosis and diagnosis and management of EoE In another aspect, the patient sample may have been previously genotyped and thus the genetic expression profile in the sample may be available to the clinician. Accordingly, the method may entail storing reference EoE associated marker sequence information in a database, i.e., those SNPs statistically associated with a more favorable or less favorable prognosis as described herein, and performance of comparative genetic analysis on the computer, thereby identifying those patients having increased risk EoE.

EoE-related SNP-containing nucleic acids, including but not limited to those listed below may be used for a variety of purposes in accordance with the present invention. EoE-associated SNP-containing DNA, RNA, or fragments thereof may be used as probes to detect the presence of and/or expression of EoE specific markers. Methods in which EoE specific marker nucleic acids may be utilized as probes for such assays include, but are not limited to: (1) in situ hybridization; (2) Southern hybridization (3) northern hybridization; and (4) assorted amplification reactions such as polymerase chain reactions (PCR).

Further, assays for detecting EoE-associated SNPs may be conducted on any type of biological sample, including but not limited to body fluids (including blood, urine, serum, gastric lavage, cerebral spinal fluid), any type of cell (such as brain cells, white blood cells, mononuclear cells, fetal cells in maternal circulation) or body tissue.

Clearly, EoE-associated SNP-containing nucleic acids, vectors expressing the same, EoE SNP-containing marker proteins and anti-EoE specific marker antibodies of the invention can be used to detect EoE associated SNPs in body tissue, cells, or fluid, and alter EoE SNP-containing marker protein expression for purposes of assessing the genetic and protein interactions involved in the development of EoE.

In most embodiments for screening for EoE-associated SNPs, the EoE-associated SNP-containing nucleic acid in the sample will initially be amplified, e.g. using PCR, to increase the amount of the templates as compared to other sequences present in the sample. This allows the target sequences to be detected with a high degree of sensitivity if they are present in the sample. This initial step may be avoided by using highly sensitive array techniques that are important in the art.

Alternatively, new detection technologies can overcome this limitation and enable analysis of small samples containing as little as 1 μg of total RNA. Using Resonance Light Scattering (RLS) technology, as opposed to traditional fluorescence techniques, multiple reads can detect low quantities of mRNAs using biotin labeled hybridized targets and anti-biotin antibodies. Another alternative to PCR amplification involves planar wave guide technology (PWG) to increase signal-to-noise ratios and reduce background interference. Both techniques are commercially available from Qiagen Inc. (USA).

Any of the aforementioned techniques may be used to detect or quantify EoE-associated SNP marker expression and accordingly, diagnose EoE.

III. Kits and Articles of Manufacture

Any of the aforementioned products can be incorporated into a kit which may contain a EoE-associated SNP specific marker polynucleotide or one or more such markers immobilized on a Gene Chip, an oligonucleotide, a polypeptide, a peptide, an antibody, a detectable label, marker, reporter, a pharmaceutically acceptable carrier, a physiologically acceptable carrier, instructions for use, a container, a vessel for administration, an assay substrate, or any combination thereof. Immobilization on a solid support refers to methods for linking the nucleic acid molecules to the support such that they cannot be stripped from the support via washing.

IV. Methods of Using EoE-Associated SNPs for the Development of Therapeutic Agents Since the SNPs identified herein have been associated with the etiology of EoE, methods for identifying agents that modulate the activity of the genes and their encoded products containing such SNPs should result in the generation of efficacious therapeutic agents for the treatment of this disorder.

Several regions of the human genome such as those listed in Table I provide suitable targets for the rational design of therapeutic agents. Small nucleic acid molecules or peptide molecules corresponding to these regions may be used to advantage in the design of therapeutic agents that effectively modulate the activity of the encoded proteins.

Molecular modeling should facilitate the identification of specific organic molecules with capacity to bind to the active site of the proteins encoded by the SNP-containing nucleic acids based on conformation or key amino acid residues required for function. A combinatorial chemistry approach will be used to identify molecules with greatest activity and then iterations of these molecules will be developed for further cycles of screening.

The polypeptides or fragments employed in drug screening assays may either be free in solution, affixed to a solid support or within a cell. One method of drug screening utilizes eukaryotic or prokaryotic host cells which are stably transformed with recombinant polynucleotides expressing the polypeptide or fragment, preferably in competitive binding assays. Such cells, either in viable or fixed form, can be used for standard binding assays. One may determine, for example, formation of complexes between the polypeptide or fragment and the agent being tested, or examine the degree to which the formation of a complex between the polypeptide or fragment and a known substrate is interfered with by the agent being tested.

Another technique for drug screening provides high throughput screening for compounds having suitable binding affinity for the encoded polypeptides and is described in detail in Geysen, PCT published application WO 84/03564, published on Sep. 13, 1984. Briefly stated, large numbers of different, small peptide test compounds, such as those described above, are synthesized on a solid substrate, such as plastic pins or some other surface. The peptide test compounds are reacted with the target polypeptide and washed. Bound polypeptide is then detected by methods well known in the art.

A further technique for drug screening involves the use of host eukaryotic cell lines or cells (such as described above) which have a nonfunctional or altered EoE associated gene. These host cell lines or cells are defective at the polypeptide level. The host cell lines or cells are grown in the presence of drug compound. Biological functions associated with the altered EoE genes are then measured to determine if the compound is capable of regulating these functions in the defective cells. Host cells contemplated for use in the present invention include but are not limited to bacterial cells, fungal cells, insect cells, mammalian cells, and plant cells. However, mammalian cells, particularly esophageal cells are preferred. The EoE-associated SNP encoding DNA molecules may be introduced singly into such host cells or in combination to assess the phenotype of cells conferred by such expression. Methods for introducing DNA molecules are also well known to those of ordinary skill in the art. Such methods are set forth in Ausubel et al. eds., Current Protocols in Molecular Biology, John Wiley & Sons, NY, N.Y. 1995, the disclosure of which is incorporated by reference herein.

A wide variety of expression vectors are available that can be modified to express the novel DNA sequences of this invention. The specific vectors exemplified herein are merely illustrative, and are not intended to limit the scope of the invention. Expression methods are described by Sambrook et al. Molecular Cloning: A Laboratory Manual or Current Protocols in Molecular Biology 16.3-17.44 (1989). Expression methods in *Saccharomyces* are also described in Current Protocols in Molecular Biology (1989).

Suitable vectors for use in practicing the invention include prokaryotic vectors such as the pNH vectors (Stratagene Inc., 11099. N. Torrey Pines Rd., La Jolla, Calif. 92037), pET vectors (Novogen Inc., 565 Science Dr., Madison, Wis. 53711) and the pGEX vectors (Pharmacia LKB Biotechnology Inc., Piscataway, N.J. 08854). Examples of eukaryotic vectors useful in practicing the present invention include the vectors pRc/CMV, pRc/RSV, and pREP (Invitrogen, 11588 Sorrento Valley Rd., San Diego, Calif. 92121); pcDNA3.1/V5&His (Invitrogen); baculovirus vectors such as pVL1392, pVL1393, or pAC360 (Invitrogen); and yeast vectors such as YRP17, YIP5, and YEP24 (New England Biolabs, Beverly, Mass.), as well as pRS403 and pRS413 Stratagene Inc.); Picchia vectors such as pHIL-D1 (Phillips Petroleum Co., Bartlesville, Okla. 74004); retroviral vectors such as PLNCX and pLPCX (Clontech); and adenoviral and adeno-associated viral vectors.

Promoters for use in expression vectors of this invention include promoters that are operable in prokaryotic or eukaryotic cells. Promoters that are operable in prokaryotic cells include lactose (lac) control elements, bacteriophage lambda (pL) control elements, arabinose control elements, tryptophan (trp) control elements, bacteriophage T7 control elements, and hybrids thereof. Promoters that are operable in eukaryotic cells include Epstein Barr virus promoters, adenovirus promoters, SV40 promoters, Rous Sarcoma Virus promoters, cytomegalovirus (CMV) promoters, baculovirus promoters such as AcMNPV polyhedrin promoter, Picchia promoters such as the alcohol oxidase promoter, and *Saccharomyces* promoters such as the ga14 inducible promoter and the PGK constitutive promoter, as well as neuronal-specific platelet-derived growth factor promoter (PDGF), the Thy-1 promoter, the hamster and mouse Prion promoter (MoPrP); and the Glial fibrillar acidic protein (GFAP) for the expression of transgenes in glial cells.

In addition, a vector of this invention may contain any one of a number of various markers facilitating the selection of a transformed host cell. Such markers include genes associated with temperature sensitivity, drug resistance, or enzymes associated with phenotypic characteristics of the host organisms.

Host cells expressing the EoE-associated SNP containing nucleic acids of the present invention or functional fragments thereof provide a system in which to screen potential compounds or agents for the ability to modulate the development of EoE. Thus, in one embodiment, the nucleic acid molecules of the invention may be used to create recombinant cell lines for use in assays to identify agents which modulate aspects of cellular metabolism associated with EoE and aberrant eosinophil function. Also provided herein are methods to screen for compounds capable of modulating the function of proteins encoded by SNP-containing nucleic acids.

Another approach entails the use of phage display libraries engineered to express fragment of the polypeptides encoded by the SNP-containing nucleic acids on the phage surface. Such libraries are then contacted with a combinatorial chemical library under conditions wherein binding affinity between the expressed peptide and the components of the chemical library may be detected. U.S. Pat. Nos. 6,057,098 and 5,965,456 provide methods and apparatus for performing such assays.

The goal of rational drug design is to produce structural analogs of biologically active polypeptides of interest or of small molecules with which they interact (e.g., agonists, antagonists, inhibitors) in order to fashion drugs which are, for example, more active or stable forms of the polypeptide, or which, e.g., enhance or interfere with the function of a polypeptide in vivo. See, e.g., Hodgson, (1991) Bio/Technology 9:19-21. In one approach, discussed above, the three-dimensional structure of a protein of interest or, for example, of the protein-substrate complex, is solved by x-ray crystallography, by nuclear magnetic resonance, by computer modeling or most typically, by a combination of approaches. Less often, useful information regarding the structure of a polypeptide may be gained by modeling based on the structure of homologous proteins. An example of rational drug design is the development of HIV protease inhibitors (Erickson et al., (1990) Science 249:527-533). In addition, peptides may be analyzed by an alanine scan (Wells, (1991) Meth. Enzym. 202:390-411). In this technique, an amino acid residue is replaced by Ala, and its effect on the peptide's activity is determined. Each of the amino acid residues of the peptide is analyzed in this manner to determine the important regions of the peptide.

It is also possible to isolate a target-specific antibody, selected by a functional assay, and then to solve its crystal structure. In principle, this approach yields a pharmacore upon which subsequent drug design can be based.

One can bypass protein crystallography altogether by generating anti-idiotypic antibodies (anti-ids) to a functional, pharmacologically active antibody. As a mirror image of a mirror image, the binding site of the anti-ids would be expected to be an analog of the original molecule. The anti-id could then be used to identify and isolate peptides from banks of chemically or biologically produced banks of peptides. Selected peptides would then act as the pharmacore.

Thus, one may design drugs which have, e.g., improved polypeptide activity or stability or which act as inhibitors, agonists, antagonists, etc. of polypeptide activity. By virtue of the availability of SNP-containing nucleic acid sequences described herein, sufficient amounts of the encoded polypeptide may be made available to perform such analytical studies as x-ray crystallography. In addition, the knowledge of the protein sequence provided herein will guide those employing computer modeling techniques in place of, or in addition to x-ray crystallography.

In another embodiment, the availability of EoE-associated SNP-containing nucleic acids enables the production of strains of laboratory mice carrying the EoE-associated SNPs of the invention. Transgenic mice expressing the EoE-associated SNP of the invention provide a model system in which to examine the role of the protein encoded by the SNP-containing nucleic acid in the development and progression towards EoE. Methods of introducing transgenes in laboratory mice are known to those of skill in the art. Three common methods include: 1. integration of retroviral vectors encoding the foreign gene of interest into an early embryo; 2. injection of DNA into the pronucleus of a newly fertilized egg; and 3. the incorporation of genetically manipulated embryonic stem cells into an early embryo. Production of the transgenic mice described above will facilitate the molecular elucidation of the role that a target protein plays in various cellular metabolic processes. Such mice provide an in vivo screening tool to study putative therapeutic drugs in a whole animal model and are encompassed by the present invention.

The term "animal" is used herein to include all vertebrate animals, except humans. It also includes an individual animal in all stages of development, including embryonic and fetal stages. A "transgenic animal" is any animal containing one or more cells bearing genetic information altered or received, directly or indirectly, by deliberate genetic manipulation at the subcellular level, such as by targeted recombination or microinjection or infection with recombinant virus. The term "transgenic animal" is not meant to encompass classical cross-breeding or in vitro fertilization, but rather is meant to encompass animals in which one or more cells are altered by or receive a recombinant DNA molecule. This molecule may be specifically targeted to a defined genetic locus, be randomly integrated within a chromosome, or it may be extrachromosomally replicating DNA. The term "germ cell line transgenic animal" refers to a transgenic animal in which the genetic alteration or genetic information was introduced into a germ line cell, thereby conferring the ability to transfer the genetic information to offspring. If such offspring, in fact, possess some or all of that alteration or genetic information, then they, too, are transgenic animals.

The alteration of genetic information may be foreign to the species of animal to which the recipient belongs, or foreign only to the particular individual recipient, or may be genetic information already possessed by the recipient. In the last case, the altered or introduced gene may be expressed differently than the native gene. Such altered or foreign genetic information would encompass the introduction of EoE-associated SNP-containing nucleotide sequences.

The DNA used for altering a target gene may be obtained by a wide variety of techniques that include, but are not limited to, isolation from genomic sources, preparation of cDNAs from isolated mRNA templates, direct synthesis, or a combination thereof.

A preferred type of target cell for transgene introduction is the embryonal stem cell (ES). ES cells may be obtained from pre-implantation embryos cultured in vitro (Evans et al., (1981) Nature 292:154-156; Bradley et al., (1984) Nature 309:255-258; Gossler et al., (1986) Proc. Natl. Acad. Sci. 83:9065-9069). Transgenes can be efficiently introduced into the ES cells by standard techniques such as DNA transfection or by retrovirus-mediated transduction. The resultant transformed ES cells can thereafter be combined with blastocysts from a non-human animal. The introduced ES cells thereafter colonize the embryo and contribute to the germ line of the resulting chimeric animal.

One approach to the problem of determining the contributions of individual genes and their expression products is to use isolated EoE-associated SNP containing genes as insertional cassettes to selectively inactivate a wild-type gene in totipotent ES cells (such as those described above) and then generate transgenic mice. The use of gene-targeted ES cells in the generation of gene-targeted transgenic mice was described, and is reviewed elsewhere (Frohman et al., (1989) Cell 56:145-147; Bradley et al., (1992) Bio/Technology 10:534-539):

Techniques are available to inactivate or alter any genetic region to a mutation desired by using targeted homologous recombination to insert specific changes into chromosomal alleles. However, in comparison with homologous extrachromosomal recombination, which occurs at a frequency approaching 100%, homologous plasmid-chromosome recombination was originally reported to only be detected at frequencies between $10^{-6}$ and $10^{-3}$. Nonhomologous plasmid-chromosome interactions are more frequent occurring at levels $10^5$-fold to $10^2$ fold greater than comparable homologous insertion.

To overcome this low proportion of targeted recombination in murine ES cells, various strategies have been developed to detect or select rare homologous recombinants. One approach for detecting homologous alteration events uses the polymerase chain reaction (PCR) to screen pools of transformant cells for homologous insertion, followed by screening of individual clones. Alternatively, a positive genetic selection approach has been developed in which a marker gene is constructed which will only be active if homologous insertion occurs, allowing these recombinants to be selected directly. One of the most powerful approaches developed for selecting homologous recombinants is the positive-negative selection (PNS) method developed for genes for which no direct selection of the alteration exists. The PNS method is more efficient for targeting genes which are not expressed at high levels because the marker gene has its own promoter. Non-homologous recombinants are selected against by using the Herpes Simplex virus thymidine kinase (HSV-TK) gene and selecting against its non-homologous insertion with effective herpes drugs such as gancyclovir (GANC) or (1-(2-deoxy-2-fluoro-B-D arabinofluranosyl)-5-iodou-racil, (FIAU). By this counter selection, the number of homologous recombinants in the surviving transformants can be increased. Utilizing EoE-associated SNP-containing nucleic acid as a targeted insertional cassette provides means to detect a successful insertion as visualized, for example, by acquisition of immunoreactivity to an antibody immunologically specific for the polypeptide encoded by EoE-associated SNP nucleic acid and, therefore, facilitates screening/selection of ES cells with the desired genotype.

As used herein, a knock-in animal is one in which the endogenous murine gene, for example, has been replaced with human EoE-associated SNP-containing gene of the invention. Such knock-in animals provide an ideal model system for studying the development of EoE.

As used herein, the expression of a EoE-associated SNP-containing nucleic acid can be targeted in a "tissue specific manner" or "cell type specific manner" using a vector in which nucleic acid sequences encoding all or a portion of an EoE-associated SNP containing nucleic acid are operably linked to regulatory sequences (e.g., promoters and/or enhancers) that direct expression of the encoded protein in a particular tissue or cell type. Such regulatory elements may be used to advantage for both in vitro and in vivo applications. Promoters for directing tissue specific proteins are well known in the art and described herein.

The nucleic acid sequence encoding the EoE-associated SNP of the invention may be operably linked to a variety of different promoter sequences for expression in transgenic animals. Such promoters include, but are not limited to a prion gene promoter such as hamster and mouse Prion promoter (MoPrP), described in U.S. Pat. No. 5,877,399 and in Borchelt et al., Genet. Anal. 13(6) (1996) pages 159-163; a rat neuronal specific enolase promoter, described in U.S. Pat. Nos. 5,612,486, and 5,387,742; a platelet-derived growth factor B gene promoter, described in U.S. Pat. No. 5,811,633; a brain specific dystrophin promoter, described in U.S. Pat. No. 5,849,999; a Thy-1 promoter; a PGK promoter; a CMV promoter; a neuronal-specific platelet-derived growth factor B gene promoter; a NEGRI promoter, a GRM5 promoter, and a promotor of any gene listed in the tables below.

Methods of use for the transgenic mice of the invention are also provided herein. Transgenic mice into which a nucleic acid containing the EoE-associated SNP or its encoded protein have been introduced are useful, for example, to develop screening methods to screen therapeutic agents to identify those capable of modulating the development of EoE.

V. Pharmaceutical and Peptide Therapies

The elucidation of the role played by the EoE associated SNP containing nucleic acids described herein facilitates the development of pharmaceutical compositions useful for treatment and diagnosis of EoE. These compositions may comprise, in addition to one of the above substances, a pharmaceutically acceptable excipient, carrier, buffer, stabilizer or other materials well known to those skilled in the art. Such materials should be non-toxic and should not interfere with the efficacy of the active ingredient. The precise nature of the carrier or other material may depend on the route of administration, e.g. oral, intravenous, cutaneous or subcutaneous, nasal, intramuscular, intraperitoneal routes.

Several treatment regimens for the treatment of EoE are known. These include, without limitation, elimination and elemental diets to decrease allergen exposure, acid suppression to treat gastroesophageal reflux disease, which may mimic or contribute to eosinophilic esophagitis, topical glucocorticoids to decrease esophageal inflammation and esophageal dilation to treat strictures. In one aspect of the invention, a test and treat method is disclosed wherein a patient is assessed for an EoE associated genetic alteration as disclosed herein and treating patients harboring such alterations with agents known to be useful for ameliorating symptoms associated with EoE.

Whether it is a polypeptide, antibody, peptide, nucleic acid molecule, small molecule or other pharmaceutically useful compound according to the present invention that is to be given to an individual, administration is preferably in a "prophylactically effective amount" or a "therapeutically effective amount" (as the case may be, although prophylaxis may be considered therapy), this being sufficient to show benefit to the individual.

The materials and methods set forth below are provided to facilitate the practice of the following examples.

Samples: The EoE discovery cohort consisted of 603 clinically confirmed EoE patients of European ancestry and 3637 matched controls. 529 samples were collected from 5 US sites, including CHOP, UCSD, Northwestern, Stanford and UCSM, the mean age of these cases was 8.75 years. A further 74 samples were collected from AMC, mean age was 39.9. The replication cohort consisted of 333 cases and 675 controls of European ancestry. The mean age of the replication cohort cases was 8.4 SD years. All cases were biopsy proven with an eosinophils/hpf (400×) count of ≥24 on proton pump inhibitor (PPI) therapy for at least 8 weeks. The majority of EoE subjects in both discovery and replication cohorts were male making up 73% in the discovery cohort and 75% in the replication cohort. Moreover, 70% of the discovery cohort and 72% of the replication cohort had asthma, allergic rhinitis or atopic dermatitis. The study was approved by the Institutional Review Board (IRB) of the Children's Hospital of Philadelphia (CHOP). Written informed consent for participation in the study was obtained from all participants and their parents or guardians.

Genotyping: The discovery samples were genotyped on either the Illumina HumanHap550, HH610 and the replication samples were genotyped on the Illumina HumanOmni Express-12v1 arrays at the Center for Applied Genomics at CHOP. Standard quality control parameters were applied to the dataset, samples with chip-wide genotyping failure rate <5% were excluded. SNPs with minor allele frequencies of <1%, genotyping failure rates of greater that 2% and Hardy-Weinberg P-Values less that $1\times10^{-6}$ were excluded from further analysis.

Genetic ancestry was determined by computing principal components on the dataset using smartpca, a part of the EIGENSTRAT package, on 100,000 random autosomal SNPs in linkage equilibrium. Samples were clustered into 4 Continental ancestry groups (Caucasian, African including admixed African-American, Asian and native American/admixed Hispanic) by K-means clustering using the kmeans package in R.

Population stratification: smartPCA eigenvectors were included as covariates in a logistic regression to control for population stratification as required. To determine the genomic inflation for each case control set, we carried out an association analysis on the genotype data using plink prior to imputation. If genomic inflation exceeded 1.03, principal components were included as covariates in the post-imputation GWAS.

Duplicate samples and cryptic relatedness: pairwise IBD values were generated for all samples using the plink genome command. IBD was performed independently on the samples of Caucasians ancestry and African ancestry. A random sample from any pair with a PI_HAT value exceeding 0.3 was excluded from further analysis.

Imputation: Imputation of untyped markers (~39M) was carried out using IMPUTE2 after prephasing with Shapeit. Each chromosome was prephased separately. To prevent chip-based batch effects due to differences in variant densities, each chip type was prephased and imputed separately. Reference phased cosmopolitan haplotypes and recombination rates were obtained from the 1000 genomes project (1000 Genomes Phase I integrated variant set b37 March 2012 release). Imputation was carried out in 5 Mb intervals using an effective population size of 20000 as recommended. As a measure of the overall imputation accuracy we compared the concordance between the imputed and known genotypes in the subset of SNPs for which genotyping data was available. At a call threshold of 0.9, over 99% of the imputed genotypes were called and over 96% of those were concordant with the known genotypes.

Post-imputation association analysis: Statistical tests for association were carried out using the SNPTESTv2 package. Single marker analyses for the genome-wide data were carried out using linear regression taking genotype uncertainty introduced by the imputation into account. Call threshold was set at 0.9. SNPs with an info score below 0.8 were excluded from further analysis; the score is a measure of the observed information for the estimate of the allele frequencies at each imputed SNP which is obtained by splitting the data into two components, observed and missing, the observed data likelihood is then integrated over the missing data. Combined P-values across the individual data sets were generated using both fixed-effect and random-effect meta-analyses as implemented in the metal package for the fixed effects and the RE2 model in the METASOFT package for the random effects.

Transcriptome sequencing: mRNA libraries were constructed from primary esophageal epithelial cells derived from 9 cases (55% male and 44% female; mean age 11.6) and 3 controls (33% male and 66% female; mean age 12.1) using the Illumina TruSeq RNA Sample Preparation Kit v2, according to the manufacturer's instructions with 12 unique indexed adapters. Libraries were sequenced on an Illumina HiSeq 2000, generating 7.5 Gb 100 bp paired-end reads per sample. Transcripts were assembled, transcript abundances estimated and tested for differential expression between cases and controls using the cufflinks package.

Pathway analysis: Differentially expressed genes from the transcriptome sequencing experiment were separated into two lists of up or down regulated genes in the cases vs controls. Inclusion criteria included a statistically significant differential expression test (P range $5\times10^{-5}$–0.0019) and a minimum two $\log_2$ fold-change. Enrichment of KEGG pathways, Gene Ontology (GO) terms and Functional categories (SP_PIR_KEYWORDS) was analyzed using DAVID (http://david.abcc.ncifcrf.gov/).

The following example is provided to illustrate certain embodiments of the invention. It is not intended to limit the invention in any way.

Example I

Here we describe the results of an expanded GWAS totaling 936 cases and 4312 controls in an imputed dataset that included ~2.3M variants, identifying four novel EoE associated loci.

EoE GWAS

Figure 2:
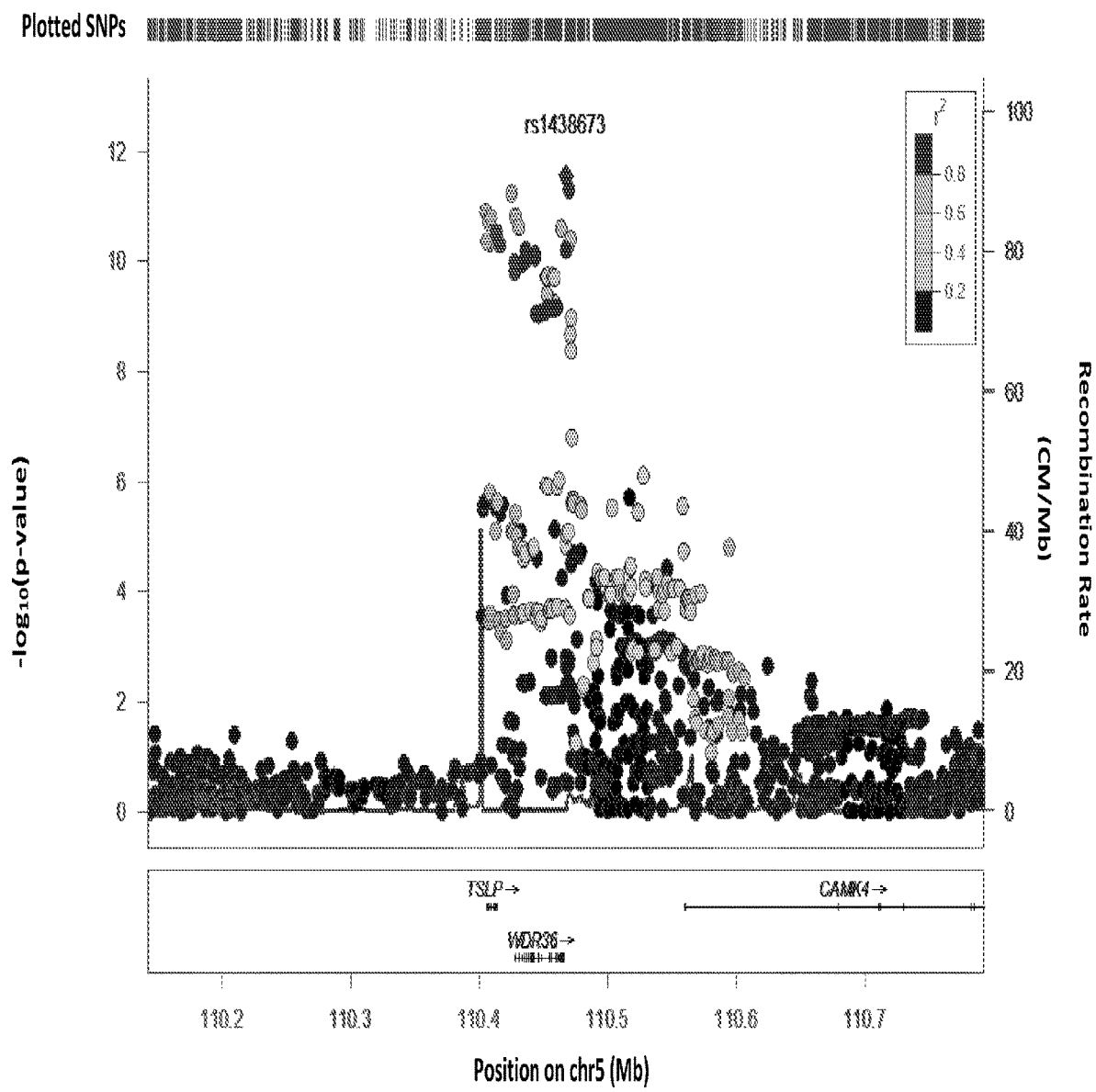
FIG. 2: Regional association plot at the TSLP locus on chr5q22.1.
Figure 3A:
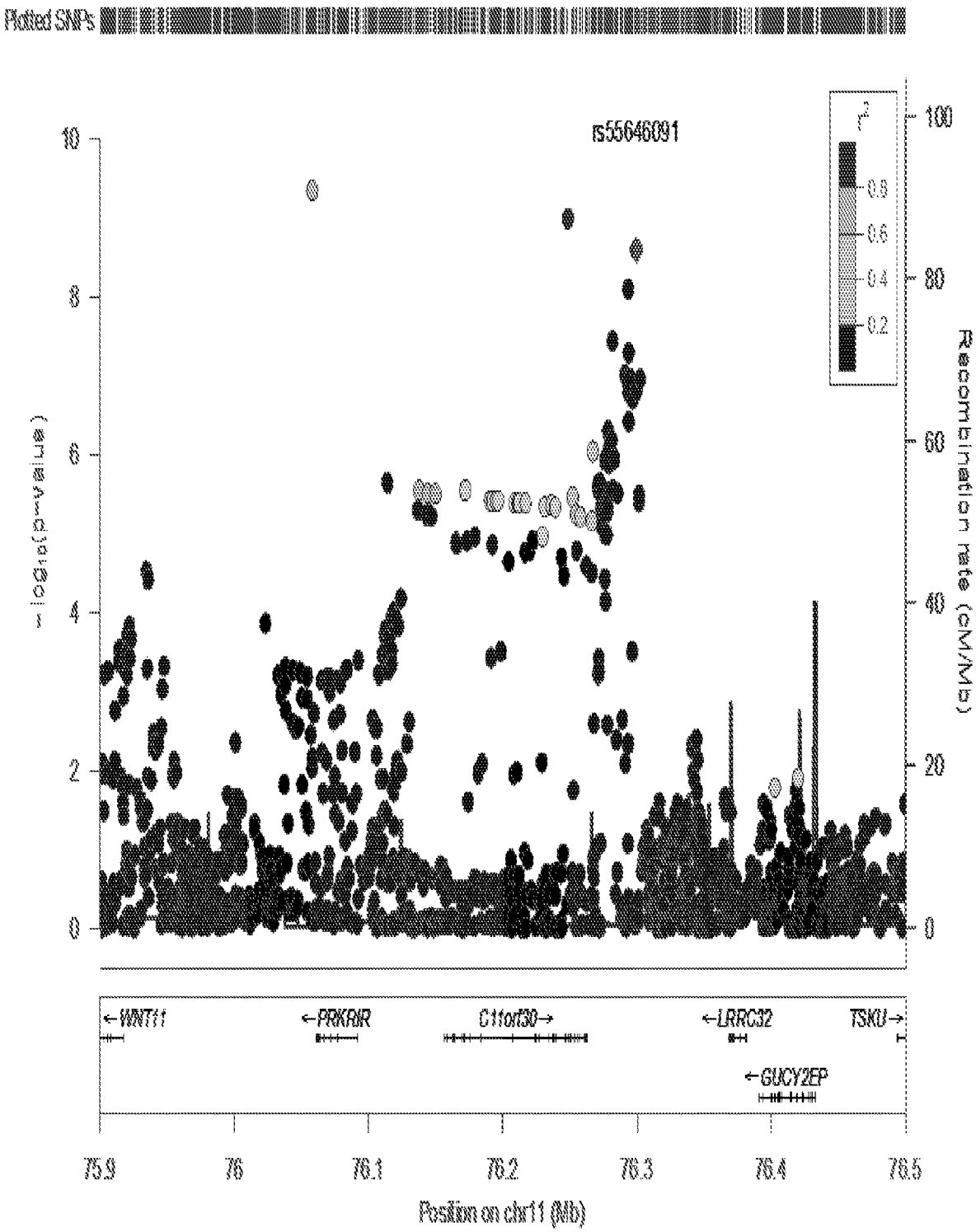
FIGS. 3A-3B: Regional association plot at the c11orf30 locus. Independent effects are clearly visible in the LD patterns of the associated variants.
Figure 3B:
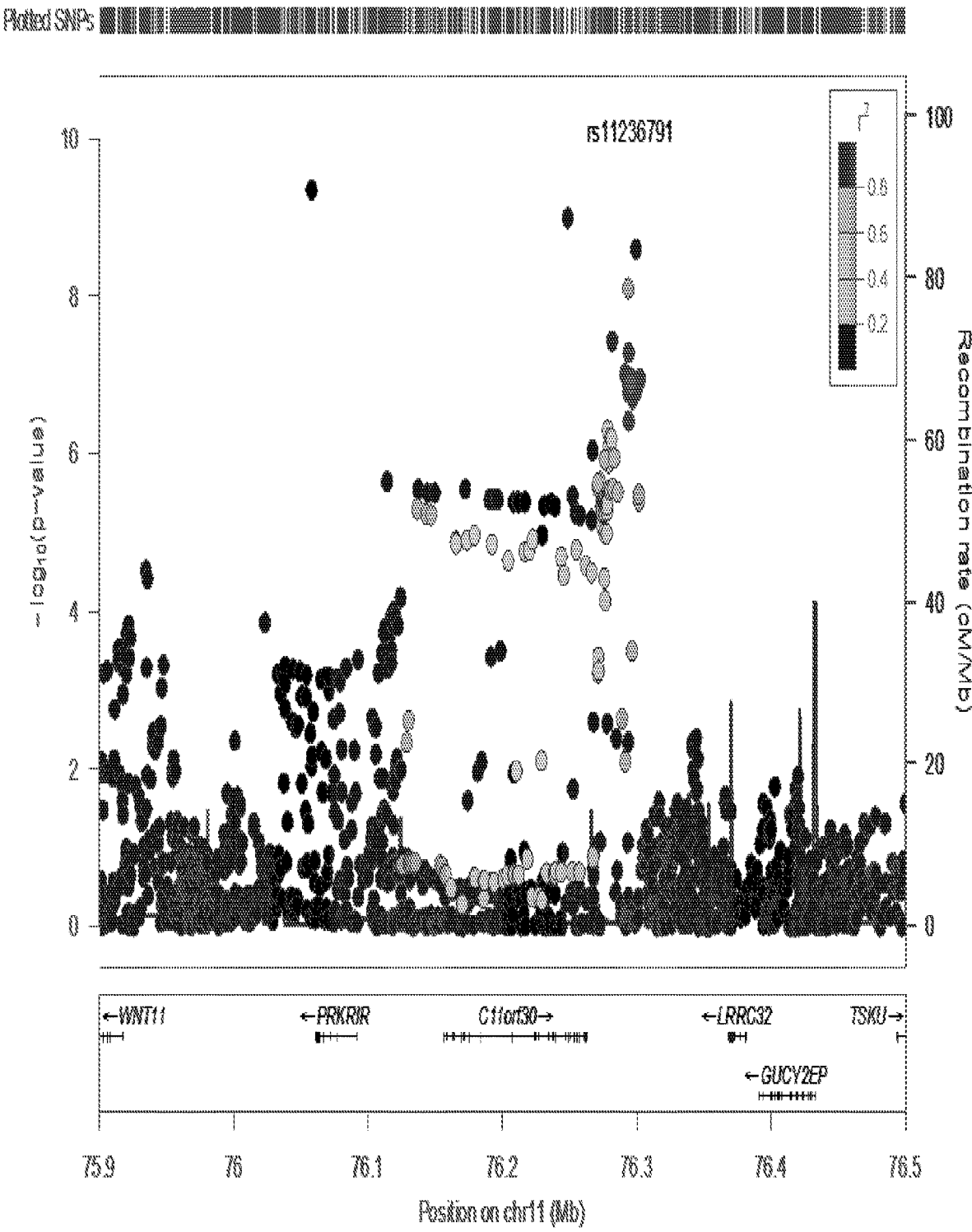
Figure 4:
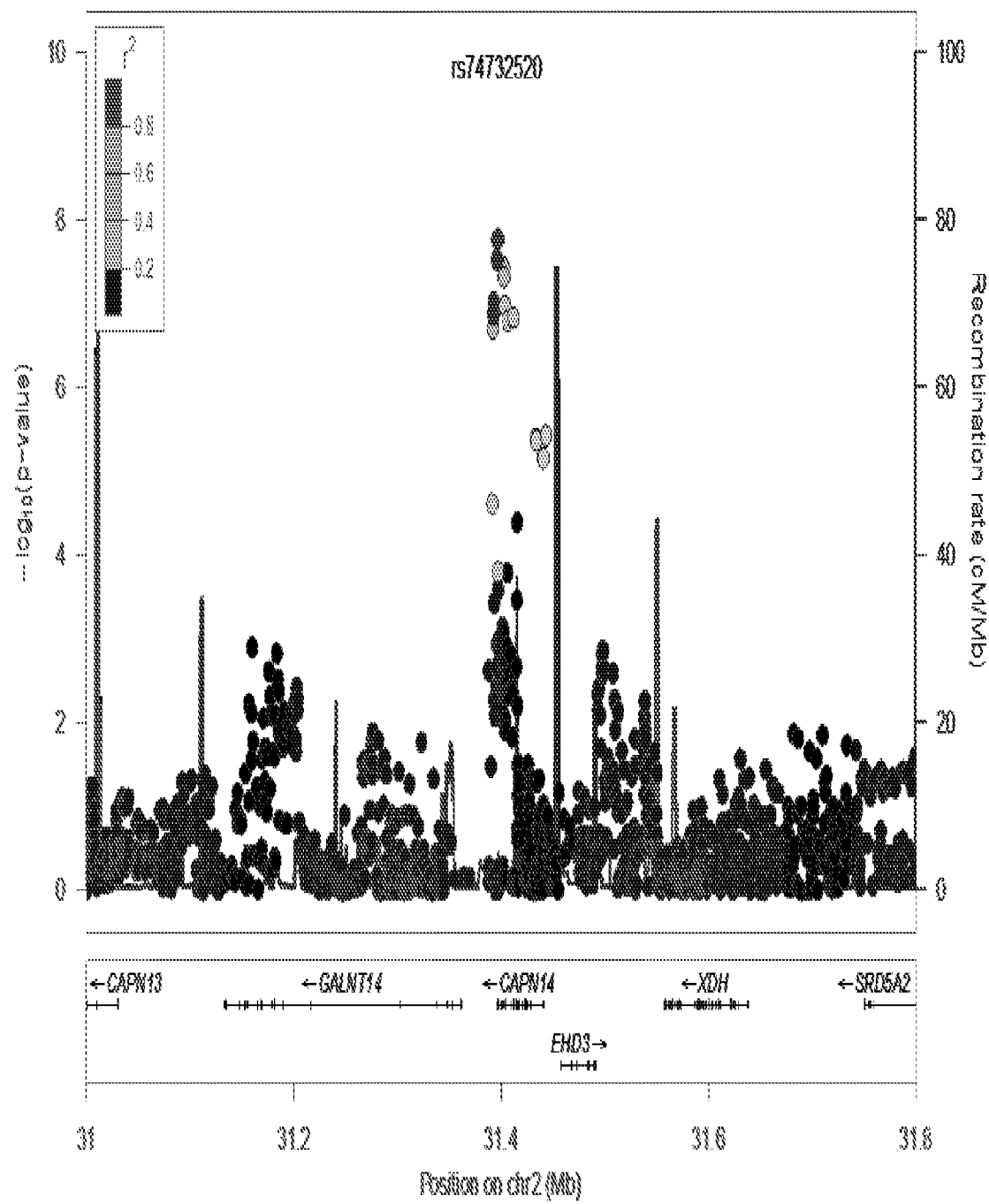
FIG. 4: Regional association plot at the CAPN14 locus on chr2p23.1
Figure 5:
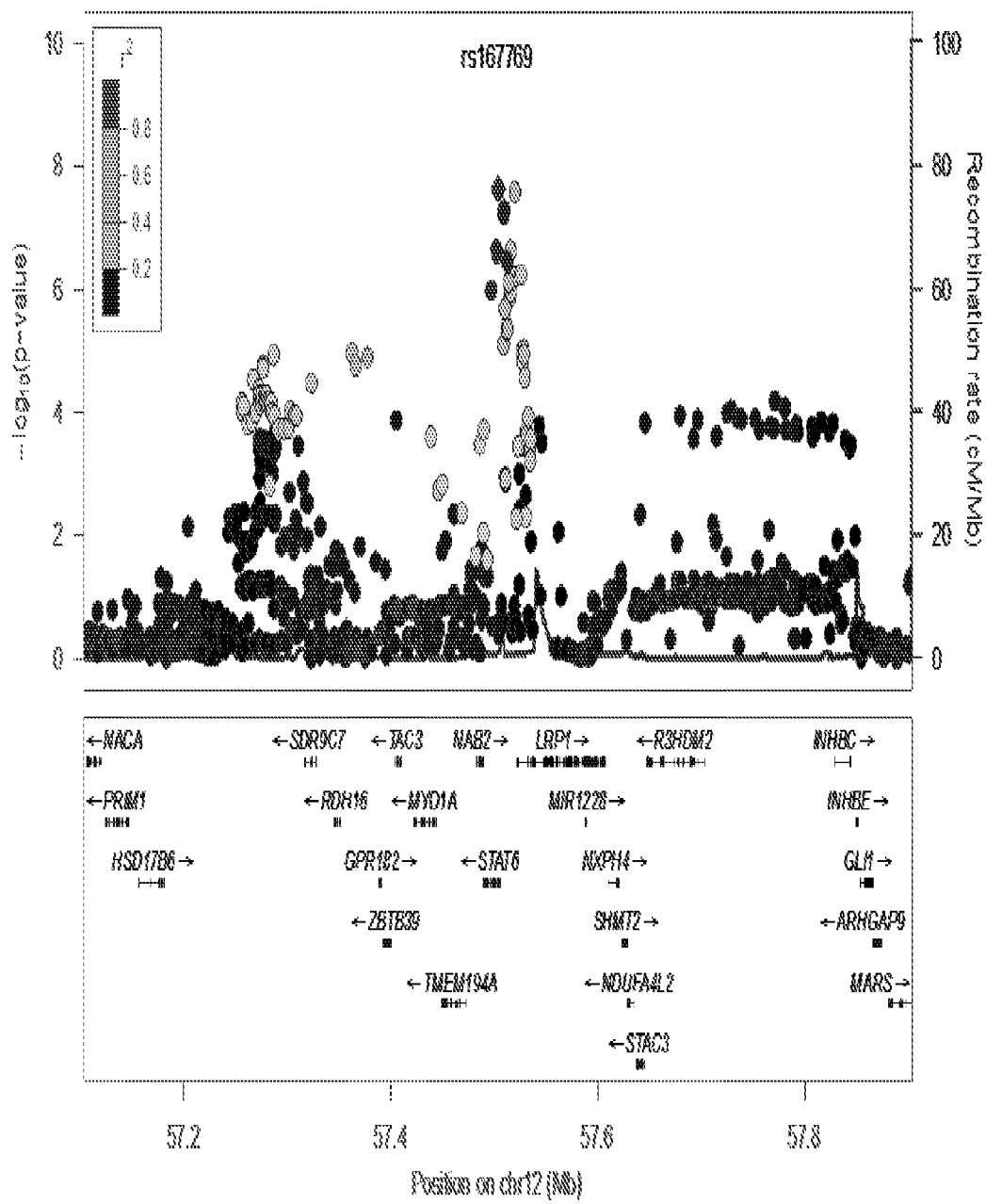
FIG. 5: Regional association plot at the STAT6 locus on chr12q13.3
Figure 6:
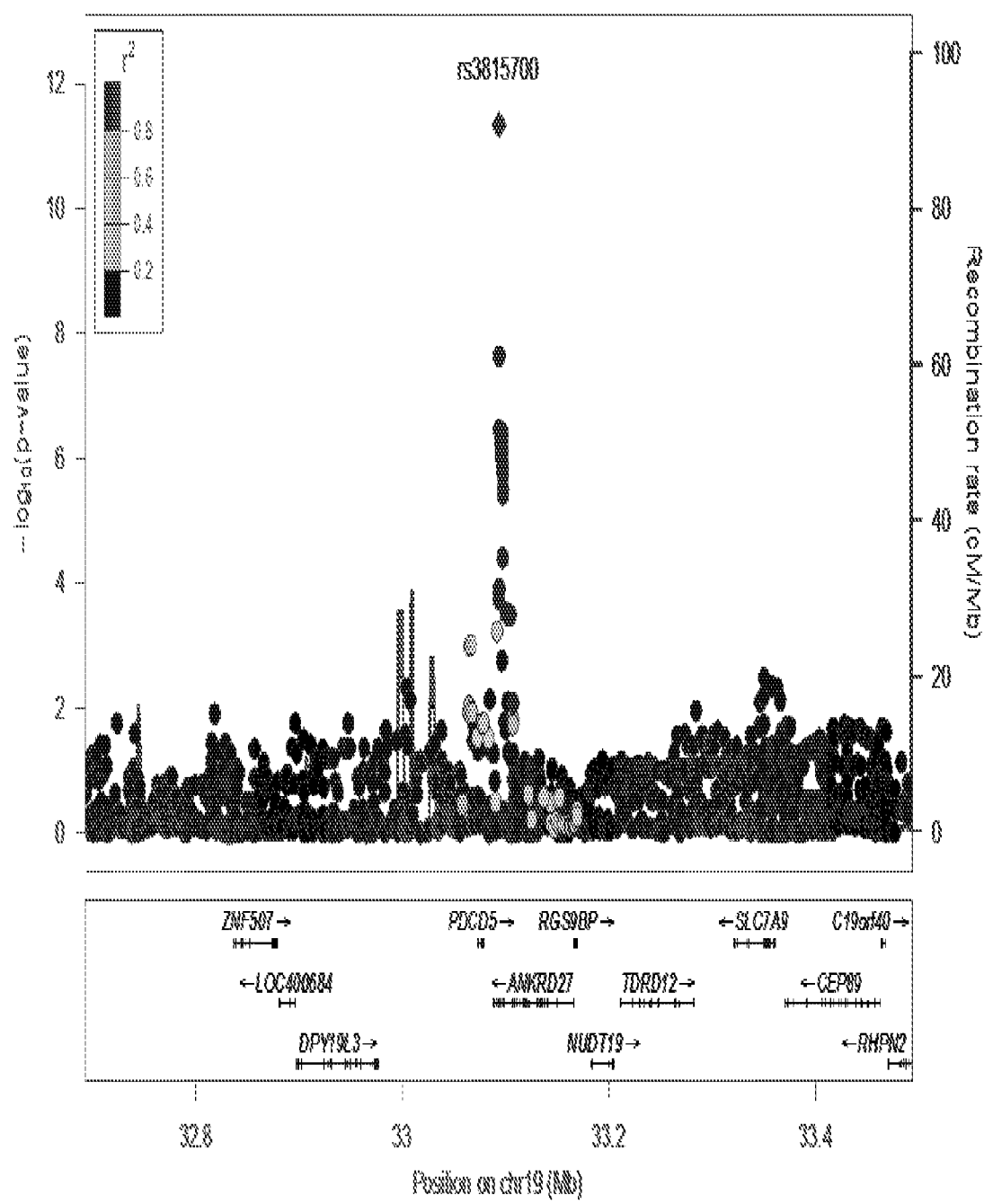
FIG. 6: Regional association plot at the ANKRD27 locus on chr19q13.11

The dataset was split into discovery and replication sets based on the Illumina arrays on which the samples were genotyped (HH550/HH610 or OmniExpress). Following GWAS of the discovery cohort (n=603 cases and 3637 controls) by logistic regression of the binary EoE phenotype adjusting for sex and the first 10 eigenvectors of the principal component analysis, five loci remained genome wide significant (cutoff $P \leq 5\times10^{-8}$) following multiple testing correction (FIG. 1). The same variants at the TSLP, c11orf30 and CAPN14 loci were also associated with EoE in the replication cohort (n=333 cases 675 controls). The genome-wide significant variants mapped to the previously reported TSLP locus[7] (top SNP discovery cohort rs1438673; P $1.74\times10^{-12}$, OR 0.62; P replication $3.84\times10^{-3}$, OR replication 0.792; P combined $1.5\times10^{-13}$, OR 0.67; Table 1, FIG. 2) a novel locus on chr11q13.5 that contains the c11orf30 gene (top SNP rs55646091; P discovery $5.83\times10^{-10}$, OR 2.21; P replication $4.33\times10^{-3}$, OR replication 1.584; P combined $7.67\times10^{-11}$, OR 2.41; FIG. 3; Table 1), and a novel locus on chr2p23.1 that spans the CAPN14 gene (top SNP rs74732520; P discovery $1.69\times10^{-8}$, OR 1.78; P replication $5.86\times10^{-3}$, OR replication 1.56; P combined $4.16\times10^{-9}$, OR 1.91; Table 1, FIG. 4). Two further novel loci surpassed genome-wide significance in the discovery cohort that we were not sufficiently powered to replicate, a locus on chr12 q13.3 that spans the STAT6 gene (top SNP rs167769, P discovery $2.29\times10^{-8}$, OR 1.49; FIG. 5) and a locus on chr19q13.11 spanning the ANKRD27 gene (top SNP rs3815700, P discovery $4.54\times10^{-12}$, OR 1.65; FIG. 6). Meta-analysis of the discovery and replication cohorts did not identify any additional genome-wide significant loci, however, a sixth intergenic locus upstream of NOVA1 at chr14q12 showed a trend towards association (top SNP rs8008716, P combined $6.9\times10^{-8}$, OR 1.71; P discovery $2.07\times10^{-6}$, OR 1.45; P replication $2.2\times10^{-3}$, OR 1.57). To determine if the c11orf30 and STAT6 signals were driven by the high rates of EoE comorbidities we carried out conditional analyses at the two loci, including asthma, atopic dermatitis and allergic rhinitis status as a covariate for the c11orf30 locus and sensitization as a covariate at the STAT6 locus in a subset of 265 cases for which we had individual level comorbidity data. Residual association with EoE was detected at both loci following the conditional analyses (Table 2).

The LD patterns between the associated variants at the c11orf30 locus indicated the presence of independent effects (FIG. 3). Conditional analyses in the discovery cohort on the top SNP, rs55646091, confirmed the existence of an independent effect, tagged by the rs11236791 variant, at the locus (Table 3).

Esophageal Biopsy Transcriptome Sequencing

RNAseq of primary epithelial cells derived from esophageal biopsy of 9 EoE patients and 3 controls confirmed expression of TSLP, c11orf30, CAPN14, STAT6, ANKRD27 and NOVA1 in esophageal epithelial cells. We detected expression of 12,407 genes out of an estimated 21,000[8]. Examining differential expression between cases and controls CAPN14 expression was almost 4 fold increased in EoE cases compared to controls (cases FPKM 9.82807, control FPKM 0.630785; log 2 (fold change) 3.96169; P $5\times10^{-5}$; Table 4). The remaining four genes showed subtle, albeit not statistically significant expression level changes. Examining other genes at the association loci, expression of both WDR36 and GALNT14 was detected but without any significant differences in cases and controls. LRRC32 was not expressed at appreciable levels (Table 4).

Pathway analysis of the differentially expressed genes in cases and controls from the transcriptome sequencing experiment indicated an enrichment of cell cycle-related GO-terms amongst genes whose expression was decreased in cases vs controls and an enrichment of epidermis and epithelial cell development and differentiation GO-terms in the list of gene whose expression increased in cases vs controls (Table 5).

DISCUSSION

Since our initial report of association of TSLP variants with EoE in under 200 patients, TSLP has been associated with allergic sensitization[9, 10], asthma[11, 12] and allergic rhinitis[13] in GWAS that required thousands of cases to achieve significance. Variants at the c11orf30 locus have been associated with seasonal allergic rhinitis[13], ulcerative colitis[14], Crohn's disease[15], atopic dermatitis[16, 17], asthma[18] and allergic sensitization[10], albeit with much lower odds ratios (range 1.09 in asthma to 1.22 in atopic dermatitis). Asthma, atopic dermatitis and allergic rhinitis are common comorbidities of EoE we therefore carried out a conditional analysis on asthma, atopic dermatitis and allergic rhinitis status in the EoE cases demonstrating that the observed c11 orf30 association with EoE was independent of comorbidity status. The c11orf30 gene encodes, EMSY, a transcriptional regulator that was initially identified as a BRCA-2-associated protein that is amplified in human mammary adenocarcinomas[19]. More recently, EMSY has been identified as a central component in a novel Akt-dependent mechanism by which IFN and other growth factors regulate the expression of interferon-stimulated genes (ISGs)[20]. STAT6 is a key player in the IL4 pathway. STAT6 when activated by IL-4, through it's receptor IL-4R, controls the expression of GATA3, the Th2 master regulatory transcription factor, as well as the 114 locus control region[21]. STAT6 has been associated with serum IgE levels[22] and allergic sensitization[10], through GWAS. Conditional analysis at the STAT6 locus on sensitization status indicated the observed association with EoE was independent of sensitization. In addition to TSLP and the c11orf30 and STAT6 loci which have previously been associated with allergic/inflammatory conditions by GWAS we identified two loci that appear to be EoE specific. The chr19 locus which spans three genes, ANKRD27, PDCD5 and RGS9BP and a locus at chr2p23.1 that spans the CAPN14 gene. CAPN14 has recently been reported to be associated with EoE following a meta analysis of 736 samples[23]. The same study also reported associations at two additional loci at XKR6 and an intergenic region on 15q13, neither of these loci showed any evidence of association in our study (XKR6 rs2898261 P 0.663; 15q13 rs8041227 P 0.5686). Of the three genes at the chr19 locus, ANKRD27 (also referred to as Varp), appears to be the most likely candidate, it has been shown to regulate the trafficking of melanogenic enzymes to epidermal melanocytes[24], interestingly, discoloration of the esophagus has recently been reported in 90% of EoE patients[25]. ANKRD27 has also recently been shown to act as a kinetic inhibitor of SNARE complex formations involving VAMP7[26], which is involved in apical transport in epithelial cells[27] and wound healing[28].

Figure 7:
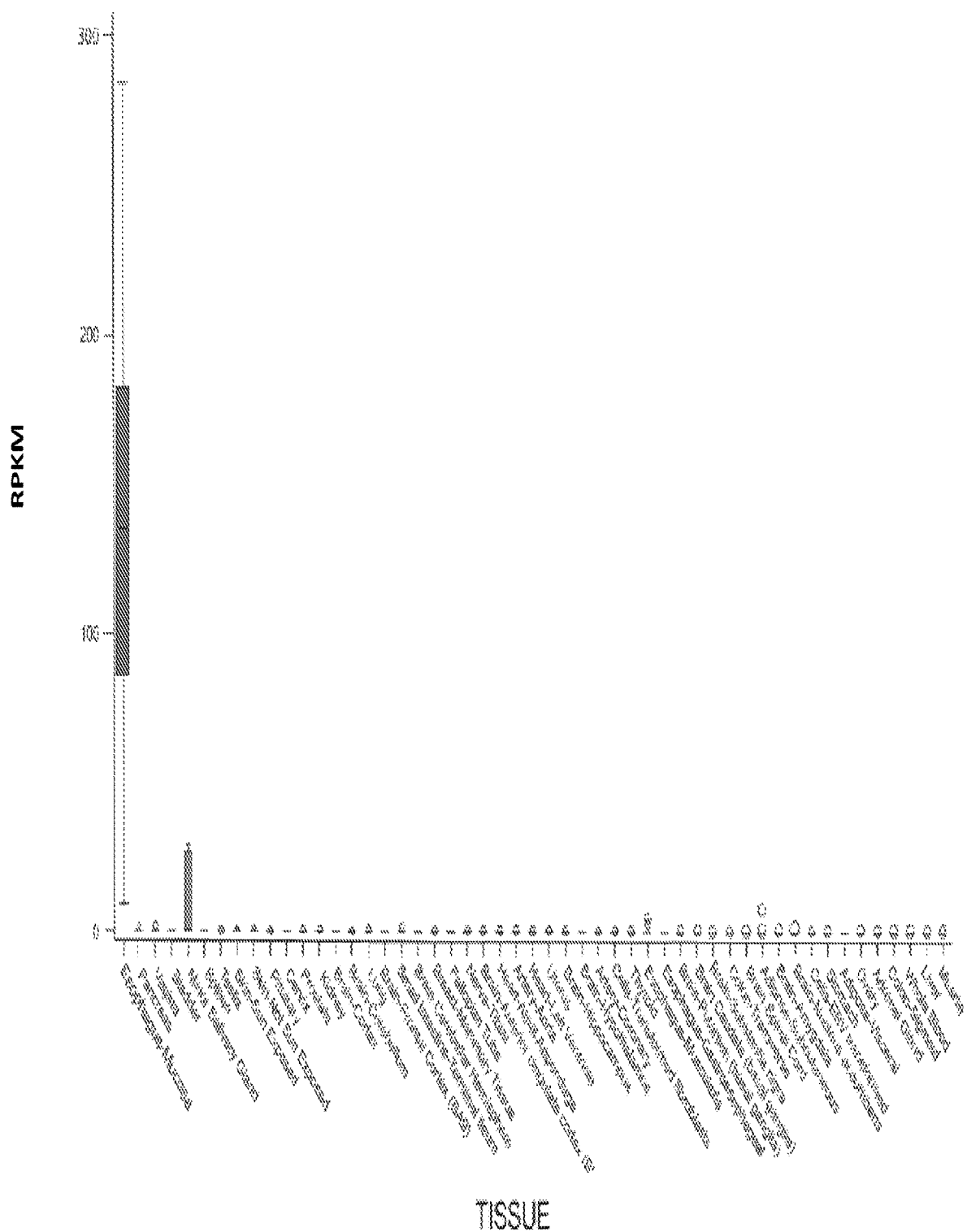
FIG. 7: CAPN14 is highly expressed in the esophagus: transcriptome sequencing data from the GTEx project indicates CAPN14 is predominantly expressed in the esophageal mucosa (n=106). Each boxplot represent a measure of CAPN14 gene expression, plotted on the y-axis for a given tissue, plotted on the x-axis. The measure of expression used is reads per kilobase million (RPKM). The boxplot whiskers represent the data range across the 106 replicates, with the notch in the box representing the median expression value.

CAPN14 is a member of the calpain family. Calpains are a family of intracellular $Ca^{2+}$-regulated cysteine proteases that have been shown to function in diverse biological processes including the cell cycle, platelet aggregation, and myoblast fusion through proteolytic cleavage of their substrates. Calpains include both ubiquitous and tissue-specific members[29], CAPN14 shows highly specific expression, initial publications did not detect expression in any tissues tested[30], however, the test panels used appear to have not included esophagus. Data from the GTEx project[31] and The Human Protein Atlas[32] both indicate that CAPN14 expression is limited to the esophageal mucosa (FIG. 7). Phylogenetically, CAPN14 is most closely related to calpain 13 and both are divergent from the remainder of the protein family. A recent evolutionary study of the calpain family indicates that CAPN14 has undergone persistent functional divergence during evolution[33].

The tissue specificity of calpains can result in tissue-specific disease phenotypes[34], mutations in CAPN3, a muscle-specific large subunit[35], result in limb-girdle muscular dystrophy, type 2A (LGMD2A)[36]. The expression of both CAPN8 and CAPN9 is predominantly restricted to the gastric surface mucus (pit) cells in the stomach. Neither gene has yet been implicated in human disease, however, mouse knock out models are susceptible to ethanol induced gastric mucosal injury, implicating both in gastric mucosal defense from external stressors[37].

Not only does CAPN14 appear to be expressed exclusively in the esophagus, our results also indicate CAPN14 is overexpressed in EoE esophageal epithelial cells compared with controls, consistent with a gain of function. Similar results have also recently been published showing upregulation of CAPN14 in primary epithelial cells from EoE biopsies and organotypic cultures after IL-13 simulation[23]. CAPN14 has previously been implicated in allergy and inflammation, it has been shown to be unregulated by IL-4 stimulation[38]. In a recent study of an asthma mouse model, inhibition of calpain by calpeptin resulted in a marked improvement of the asthma phenotype, reversing airway hyper-responsiveness, reducing airway inflammation, bronchoalveolar lavage (BAL) fluid eosinophilia, sub-epithelial fibrosis and the inflammatory cytokine profile, including IL-4, IL-5, IL-13, transforming growth factor (TGF)-β1 and ova-specific immunoglobulin E[39]. Inhibition of CAPN14 activity may therefore constitute a potential therapy for the most debilitating aspect of EoE, esophageal inflammation and remodeling.

REFERENCES

1. Furuta G T, et al. Eosinophilic esophagitis in children and adults: a systematic review and consensus recommendations for diagnosis and treatment. *Gastroenterology* 133, 1342-1363 (2007).
2. Spergel J M, et al. 14 years of eosinophilic esophagitis: clinical features and prognosis. *J Pediatr Gastroenterol Nutr* 48, 30-36 (2009).
3. Spergel J M. Eosinophilic esophagitis in adults and children: evidence for a food allergy component in many patients. *Curr Opin Allergy Clin Immunol* 7, 274-278 (2007).
4. Blanchard C, et al. IL-13 involvement in eosinophilic esophagitis: transcriptome analysis and reversibility with glucocorticoids. *J Allergy Clin Immunol* 120, 1292-1300 (2007).
5. Noel R J, Putnam P E, Rothenberg M E. Eosinophilic esophagitis. *The New England journal of medicine* 351, 940-941 (2004).
6. Johansson S G, et al. Revised nomenclature for allergy for global use: Report of the Nomenclature Review Committee of the World Allergy Organization, October 2003. *J Allergy Clin Immunol* 113, 832-836 (2004).
7. Rothenberg M E, et al. Common variants at 5q22 associate with pediatric eosinophilic esophagitis. *Nature genetics* 42, 289-291 (2010).
8. Pennisi E. Genomics. ENCODE project writes eulogy for junk DNA. *Science* 337, 1159, 1161 (2012).
9. Hinds D A, et al. A genome-wide association meta-analysis of self-reported allergy identifies shared and allergy-specific susceptibility loci. *Nat Genet* 45, 907-911 (2013).
10. Bonnelykke K, et al. Meta-analysis of genome-wide association studies identifies ten loci influencing allergic sensitization. *Nat Genet* 45, 902-906 (2013).
11. Hirota T, et al. Genome-wide association study identifies three new susceptibility loci for adult asthma in the Japanese population. *Nat Genet* 43, 893-896 (2011).
12. Torgerson D G, et al. Meta-analysis of genome-wide association studies of asthma in ethnically diverse North American populations. *Nat Genet* 43, 887-892 (2011).
13. Ramasamy A, et al. A genome-wide meta-analysis of genetic variants associated with allergic rhinitis and grass sensitization and their interaction with birth order. *J Allergy Clin Immunol* 128, 996-1005 (2011).
14. Anderson C A, et al. Meta-analysis identifies 29 additional ulcerative colitis risk loci, increasing the number of confirmed associations to 47. *Nat Genet* 43, 246-252 (2011).
15. Barrett J C, et al. Genome-wide association defines more than 30 distinct susceptibility loci for Crohn's disease. *Nat Genet* 40, 955-962 (2008).
16. Esparza-Gordillo J, et al. A common variant on chromosome 11q13 is associated with atopic dermatitis. *Nat Genet* 41, 596-601 (2009).
17. Hirota T, et al. Genome-wide association study identifies eight new susceptibility loci for atopic dermatitis in the Japanese population. *Nat Genet* 44, 1222-1226 (2012).
18. Ferreira M A, et al. Identification of IL6R and chromosome 11q13.5 as risk loci for asthma. *Lancet* 378, 1006-1014 (2011).

19. Hughes-Davies L, et al. EMSY links the BRCA2 pathway to sporadic breast and ovarian cancer. *Cell* 115, 523-535 (2003).
20. Ezell S A, et al. The protein kinase Akt1 regulates the interferon response through phosphorylation of the transcriptional repressor EMSY. *Proc Natl Acad Sci USA* 109, E613-621 (2012).
21. Ansel K M, Djuretic I, Tanasa B, Rao A. Regulation of Th2 differentiation and 114 locus accessibility. *Annual review of immunology* 24, 607-656 (2006).
22. Granada M, et al. A genome-wide association study of plasma total IgE concentrations in the Framingham Heart Study. *J Allergy Clin Immunol* 129, 840-845 e821 (2012).
23. Kottyan L C, et al. Genome-wide association analysis of eosinophilic esophagitis provides insight into the tissue specificity of this allergic disease. *Nat Genet* 46, 895-900 (2014).
24. Tamura K, Ohbayashi N, Maruta Y, Kanno E, Itoh T, Fukuda M. Varp is a novel Rab32/38-binding protein that regulates Tyrp1 trafficking in melanocytes. *Mol Biol Cell* 20, 2900-2908 (2009).
25. Tanaka K, et al. Narrow-band imaging magnifying endoscopy in adult patients with eosinophilic esophagitis/esophageal eosinophilia and lymphocytic esophagitis. *Gastrointest Endosc* 78, 659-664 (2013).
26. Schafer I B, et al. The binding of Varp to VAMP7 traps VAMP7 in a closed, fusogenically inactive conformation. *Nature structural & molecular biology* 19, 1300-1309 (2012).
27. Chaineau M, Danglot L, Galli T. Multiple roles of the vesicular-SNARE TI-VAMP in post-Golgi and endosomal trafficking. *FEBS Lett* 583, 3817-3826 (2009).
28. Rao S K, Huynh C, Proux-Gillardeaux V, Galli T, Andrews N W. Identification of SNAREs involved in synaptotagmin VII-regulated lysosomal exocytosis. *J Biol Chem* 279, 20471-20479 (2004).
29. Suzuki K, Hata S, Kawabata Y, Sorimachi H. Structure, activation, and biology of calpain. *Diabetes* 53 Suppl 1, S12-18 (2004).
30. Dear T N, Boehm T. Identification and characterization of two novel calpain large subunit genes. *Gene* 274, 245-252 (2001).
31. Consortium G T. The Genotype-Tissue Expression (GTEx) project. *Nat Genet* 45, 580-585 (2013).
32. Uhlen M, et al. Towards a knowledge-based Human Protein Atlas. *Nat Biotechnol* 28, 1248-1250 (2010).
33. Macqueen D J, Wilcox A H. Characterization of the definitive classical calpain family of vertebrates using phylogenetic, evolutionary and expression analyses. *Open biology* 4, 130219 (2014).
34. Sorimachi H, Hata S, Ono Y. Calpain chronicle—an enzyme family under multidisciplinary characterization. *Proceedings of the Japan Academy Series B, Physical and biological sciences* 87, 287-327 (2011).
35. Sorimachi H, et al. Molecular cloning of a novel mammalian calcium-dependent protease distinct from both m- and mu-types. Specific expression of the mRNA in skeletal muscle. *J Biol Chem* 264, 20106-20111 (1989).
36. Richard I, et al. Mutations in the proteolytic enzyme calpain 3 cause limb-girdle muscular dystrophy type 2A. *Cell* 81, 27-40 (1995).
37. Hata S, et al. Calpain 8/nCL-2 and calpain 9/nCL-4 constitute an active protease complex, G-calpain, involved in gastric mucosal defense. *PLoS Genet* 6, e1001040 (2010).
38. Ueta M, Sotozono C, Kinoshita S. Expression of interleukin-4 receptor alpha in human corneal epithelial cells. *Japanese journal of ophthalmology* 55, 405-410 (2011).
39. Aich J, Mabalirajan U, Ahmad T, Agrawal A, Ghosh B. Loss-of-function of inositol polyphosphate-4-phosphatase reversibly increases the severity of allergic airway inflammation. *Nature communications* 3, 877 (2012).

While certain of the preferred embodiments of the present invention have been described and specifically exemplified above, it is not intended that the invention be limited to such embodiments. It will be apparent to one skilled in the art that various changes and modifications can be made therein without departing from the scope of the present invention, as set forth in the following claims.

TABLE 1

Genome-wide significant variants: Discovery, replication and meta-analysis ORs and Pvals P values for the discovery analysis are shown in bold if directly genotyped. P values for the discovery and replication sets were generated using a missing data likelihood score test as implemented in SNPTEST2. Cutoffs, genome-wide significance ($P < 5 \times 10^{-8}$), MAF $\geq 3\%$, info scores $\geq 0.8$. $P_{het}$, heterogeneity P value for Cochrane's Q statistic. OR, odds ratio.

| Variant [Effect Allele] | chr:pos hg19 | Gene | Discovery | | | | Replication | | | | Meta | | | |
|---|---|---|---|---|---|---|---|---|---|---|---|---|---|---|
| | | | effect allele MAF | OR | Pval | SE | effect allele MAF | OR | Pval | SE | OR | SE | Pval | $P_{het}$ |
| rs78464756[G] | chr2:31396059 | CAPN14 | 0.067 | 1.767 | $2.96 \times 10^{-8}$ | 0.131 | 0.079 | 1.569 | $5.42 \times 10^{-3}$ | 0.181 | 1.904 | 0.111 | $5.927 \times 10^{-9}$ | 0.333 |
| rs74732520[G] | chr2:31396392 | CAPN14 | 0.067 | 1.782 | $1.69 \times 10^{-8}$ | 0.131 | 0.079 | 1.561 | $5.87 \times 10^{-3}$ | 0.182 | 1.917 | 0.111 | $4.166 \times 10^{-9}$ | 0.301 |
| rs143457388[A] | chr2:31402370 | CAPN14 | 0.052 | 1.858 | $3.66 \times 10^{-8}$ | 0.149 | 0.056 | 1.726 | $6.36 \times 10^{-4}$ | 0.219 | 2.215 | 0.129 | $6.061 \times 10^{-10}$ | 0.787 |
| rs149864795[A] | chr2:31402407 | CAPN14 | 0.052 | 1.846 | $4.74 \times 10^{-8}$ | 0.149 | 0.057 | 1.759 | $4.41 \times 10^{-4}$ | 0.218 | 2.216 | 0.128 | $5.245 \times 10^{-10}$ | 0.861 |
| rs10455025[C] | chr5:110404999 | TSLP | 0.356 | 1.537 | $1.21 \times 10^{-11}$ | 0.067 | 0.354 | 1.276 | $2.76 \times 10^{-3}$ | 0.102 | 1.511 | 0.057 | $4.275 \times 10^{-13}$ | 0.233 |
| rs3806932[G] | chr5:110405675 | TSLP | 0.444 | 0.630 | $4.31 \times 10^{-11}$ | 0.064 | 0.437 | 0.720 | $7.00 \times 10^{-4}$ | 0.100 | 0.671 | 0.055 | $2.706 \times 10^{-13}$ | 0.502 |
| rs3806933[T] | chr5:110406742 | TSLP | 0.439 | 0.628 | $1.88 \times 10^{-10}$ | 0.064 | 0.418 | 0.713 | $1.00 \times 10^{-3}$ | 0.101 | 0.668 | 0.055 | $1.829 \times 10^{-13}$ | 0.419 |
| rs1898671[T] | chr5:110406800 | TSLP | 0.350 | 1.514 | $4.54 \times 10^{-11}$ | 0.068 | 0.348 | 1.255 | $5.01 \times 10^{-3}$ | 0.104 | 1.499 | 0.058 | $2.826 \times 10^{-13}$ | 0.213 |
| rs2289277[G] | chr5:110409067 | TSLP | 0.437 | 0.626 | $1.57 \times 10^{-11}$ | 0.064 | 0.421 | 0.724 | $1.45 \times 10^{-3}$ | 0.101 | 0.669 | 0.055 | $2.336 \times 10^{-13}$ | 0.358 |
| rs10073816[A] | chr5:110413489 | TSLP | 0.442 | 0.628 | $3.03 \times 10^{-11}$ | 0.064 | 0.434 | 0.719 | $6.70 \times 10^{-4}$ | 0.100 | 0.668 | 0.055 | $1.873 \times 10^{-13}$ | 0.488 |
| rs6594497[T] | chr5:110418868 | TSLP | 0.441 | 0.631 | $4.92 \times 10^{-11}$ | 0.064 | 0.433 | 0.733 | $1.16 \times 10^{-3}$ | 0.100 | 0.674 | 0.055 | $5.262 \times 10^{-13}$ | 0.432 |
| rs252716[C] | chr5:110425063 | TSLP | 0.447 | 1.545 | $5.65 \times 10^{-12}$ | 0.065 | 0.454 | 1.361 | $6.65 \times 10^{-5}$ | 0.101 | 1.516 | 0.055 | $4.053 \times 10^{-14}$ | 0.389 |
| rs10050834[T] | chr5:110427328 | TSLP | 0.452 | 0.639 | $1.03 \times 10^{-10}$ | 0.064 | 0.437 | 0.749 | $1.59 \times 10^{-3}$ | 0.101 | 0.680 | 0.054 | $1.418 \times 10^{-12}$ | 0.448 |
| rs7723819[A] | chr5:110427347 | TSLP | 0.453 | 0.641 | $1.54 \times 10^{-10}$ | 0.064 | 0.441 | 0.739 | $1.05 \times 10^{-3}$ | 0.101 | 0.680 | 0.054 | $1.341 \times 10^{-12}$ | 0.524 |
| rs79881201[T] | chr5:110427795 | TSLP | 0.362 | 1.536 | $1.48 \times 10^{-11}$ | 0.067 | 0.367 | 1.250 | $5.45 \times 10^{-3}$ | 0.102 | 1.495 | 0.057 | $1.123 \times 10^{-12}$ | 0.184 |
| rs17623144[G] | chr5:110430488 | TSLP | 0.360 | 1.532 | $2.37 \times 10^{-11}$ | 0.067 | 0.361 | 1.261 | $3.35 \times 10^{-3}$ | 0.103 | 1.498 | 0.057 | $9.369 \times 10^{-13}$ | 0.248 |
| rs1993465[G] | chr5:110433098 | TSLP | 0.456 | 0.640 | $1.08 \times 10^{-10}$ | 0.064 | 0.444 | 0.748 | $1.42 \times 10^{-3}$ | 0.101 | 0.679 | 0.055 | $1.318 \times 10^{-12}$ | 0.462 |
| rs6859041[A] | chr5:110435231 | TSLP | 0.455 | 0.639 | $9.85 \times 10^{-11}$ | 0.064 | 0.444 | 0.744 | $1.39 \times 10^{-3}$ | 0.101 | 0.679 | 0.055 | $1.186 \times 10^{-12}$ | 0.457 |
| rs1379298[C] | chr5:110435726 | TSLP | 0.455 | 0.639 | $6.16 \times 10^{-11}$ | 0.064 | 0.444 | 0.752 | $1.79 \times 10^{-3}$ | 0.101 | 0.677 | 0.055 | $1.005 \times 10^{-12}$ | 0.405 |
| rs10038177[T] | chr5:110436450 | TSLP | 0.457 | 0.638 | $9.00 \times 10^{-11}$ | 0.064 | 0.445 | 0.755 | $2.19 \times 10^{-3}$ | 0.100 | 0.681 | 0.054 | $1.785 \times 10^{-12}$ | 0.389 |
| rs6865932[C] | chr5:110436852 | TSLP | 0.457 | 0.638 | $8.79 \times 10^{-11}$ | 0.064 | 0.445 | 0.752 | $1.90 \times 10^{-3}$ | 0.100 | 0.680 | 0.054 | $1.501 \times 10^{-12}$ | 0.405 |
| chr5:110437826:I[TA] | chr5:110437826 | TSLP | 0.361 | 1.539 | $1.72 \times 10^{-11}$ | 0.066 | 0.365 | 1.256 | $5.71 \times 10^{-3}$ | 0.102 | 1.492 | 0.056 | $1.329 \times 10^{-12}$ | 0.189 |
| chr5:110437828:I[AT] | chr5:110437828 | TSLP | 0.361 | 1.539 | $1.68 \times 10^{-11}$ | 0.067 | 0.364 | 1.248 | $5.68 \times 10^{-3}$ | 0.102 | 1.493 | 0.057 | $1.297 \times 10^{-12}$ | 0.188 |
| rs10045255[G] | chr5:110438357 | TSLP | 0.458 | 0.637 | $7.68 \times 10^{-11}$ | 0.064 | 0.446 | 0.765 | $3.13 \times 10^{-3}$ | 0.100 | 0.683 | 0.054 | $2.297 \times 10^{-12}$ | 0.335 |
| rs1379300[C] | chr5:110441439 | TSLP | 0.457 | 0.638 | $7.81 \times 10^{-11}$ | 0.064 | 0.444 | 0.741 | $1.41 \times 10^{-3}$ | 0.100 | 0.678 | 0.054 | $9.752 \times 10^{-13}$ | 0.440 |
| rs2034896[A] | chr5:110441533 | TSLP | 0.457 | 0.638 | $7.79 \times 10^{-11}$ | 0.064 | 0.444 | 0.741 | $1.41 \times 10^{-3}$ | 0.100 | 0.678 | 0.054 | $9.755 \times 10^{-13}$ | 0.439 |
| rs10043631[T] | chr5:110443228 | TSLP | 0.457 | 0.637 | $7.24 \times 10^{-11}$ | 0.064 | 0.445 | 0.745 | $1.77 \times 10^{-3}$ | 0.100 | 0.679 | 0.054 | $1.166 \times 10^{-12}$ | 0.406 |
| rs10038058[G] | chr5:110443281 | TSLP | 0.456 | 0.639 | $8.63 \times 10^{-11}$ | 0.064 | 0.445 | 0.745 | $1.77 \times 10^{-3}$ | 0.100 | 0.680 | 0.054 | $1.372 \times 10^{-12}$ | 0.413 |
| rs13178997[T] | chr5:110444249 | TSLP | 0.441 | 0.654 | $8.80 \times 10^{-11}$ | 0.064 | 0.435 | 0.710 | $2.96 \times 10^{-4}$ | 0.100 | 0.681 | 0.054 | $2.003 \times 10^{-12}$ | 0.815 |
| rs13161853[A] | chr5:110446741 | TSLP | 0.441 | 0.654 | $8.96 \times 10^{-11}$ | 0.064 | 0.432 | 0.709 | $2.88 \times 10^{-4}$ | 0.100 | 0.681 | 0.055 | $1.987 \times 10^{-12}$ | 0.823 |
| chr5:110449140:I[CT] | chr5:110449140 | TSLP | 0.439 | 0.654 | $6.46 \times 10^{-10}$ | 0.064 | 0.437 | 0.716 | $3.49 \times 10^{-4}$ | 0.101 | 0.679 | 0.055 | $1.745 \times 10^{-12}$ | 0.764 |
| rs2112541[C] | chr5:110449346 | TSLP | 0.441 | 0.653 | $8.17 \times 10^{-10}$ | 0.064 | 0.437 | 0.726 | $6.11 \times 10^{-4}$ | 0.100 | 0.684 | 0.055 | $3.757 \times 10^{-12}$ | 0.692 |
| rs10060003[G] | chr5:110449357 | TSLP | 0.441 | 0.653 | $8.17 \times 10^{-10}$ | 0.064 | 0.437 | 0.726 | $6.11 \times 10^{-4}$ | 0.100 | 0.684 | 0.055 | $3.757 \times 10^{-12}$ | 0.692 |
| rs10055177[G] | chr5:110450584 | TSLP | 0.441 | 0.653 | $8.07 \times 10^{-10}$ | 0.064 | 0.437 | 0.724 | $5.91 \times 10^{-4}$ | 0.100 | 0.684 | 0.055 | $3.6 \times 10^{-12}$ | 0.694 |
| rs6880351[G] | chr5:110451664 | TSLP | 0.441 | 0.653 | $8.00 \times 10^{-10}$ | 0.064 | 0.436 | 0.731 | $8.92 \times 10^{-4}$ | 0.100 | 0.686 | 0.055 | $5.367 \times 10^{-12}$ | 0.629 |
| rs6881147[C] | chr5:110451936 | TSLP | 0.441 | 0.653 | $7.82 \times 10^{-10}$ | 0.064 | 0.436 | 0.728 | $6.60 \times 10^{-4}$ | 0.100 | 0.685 | 0.055 | $3.888 \times 10^{-12}$ | 0.676 |
| rs6884870[G] | chr5:110452084 | TSLP | 0.350 | 1.501 | $1.88 \times 10^{-10}$ | 0.068 | 0.352 | 1.218 | 0.013 | 0.105 | 1.468 | 0.058 | $2.988 \times 10^{-11}$ | 0.176 |
| rs10059658[C] | chr5:110452815 | TSLP | 0.438 | 0.649 | $3.92 \times 10^{-10}$ | 0.064 | 0.435 | 0.726 | $5.39 \times 10^{-4}$ | 0.100 | 0.679 | 0.055 | $1.663 \times 10^{-12}$ | 0.658 |
| rs10051830[A] | chr5:110452845 | TSLP | 0.441 | 0.653 | $7.02 \times 10^{-10}$ | 0.064 | 0.435 | 0.722 | $4.54 \times 10^{-4}$ | 0.100 | 0.682 | 0.055 | $2.433 \times 10^{-12}$ | 0.727 |
| rs77793850[A] | chr5:110452944 | TSLP | 0.350 | 1.502 | $1.88 \times 10^{-10}$ | 0.068 | 0.350 | 1.219 | 0.011 | 0.105 | 1.470 | 0.058 | $2.471 \times 10^{-11}$ | 0.191 |
| rs17624321[G] | chr5:110453076 | TSLP | 0.350 | 1.502 | $1.85 \times 10^{-10}$ | 0.068 | 0.352 | 1.218 | 0.012 | 0.105 | 1.469 | 0.058 | $2.701 \times 10^{-11}$ | 0.184 |

TABLE 1-continued

Genome-wide significant variants: Discovery, replication and meta-analysis ORs and Pvals P values for the discovery analysis are shown in bold if directly genotyped. P values for the discovery and replication sets were generated using a missing data likelihood score test as implemented in SNPTEST2. Cutoffs, genome-wide significance ($P < 5 \times 10^{-8}$), MAF ≥ 3%, info scores ≥ 0.8. $P_{het}$, heterogeneity P value for Cochrane's Q statistic. OR, odds ratio.

| Variant [Effect Allele] | chr:pos hg19 | Gene | Discovery effect allele MAF | OR | SE | Pval | Replication effect allele MAF | OR | SE | Pval | Meta OR | SE | Pval | $P_{het}$ |
|---|---|---|---|---|---|---|---|---|---|---|---|---|---|---|
| rs7732974[C] | chr5:110455381 | TSLP | 0.441 | 0.653 | 0.064 | $7.21 \times 10^{-10}$ | 0.435 | 0.725 | 0.100 | $5.28 \times 10^{-4}$ | 0.683 | 0.055 | $2.888 \times 10^{-12}$ | 0.707 |
| rs17624673[T] | chr5:110457158 | TSLP | 0.350 | 1.503 | 0.068 | $1.86 \times 10^{-10}$ | 0.352 | 1.218 | 0.105 | 0.012 | 1.469 | 0.058 | $2.715 \times 10^{-11}$ | 0.184 |
| rs6594498[A] | chr5:110458351 | TSLP | 0.441 | 0.653 | 0.064 | $7.08 \times 10^{-10}$ | 0.432 | 0.716 | 0.101 | $3.32 \times 10^{-4}$ | 0.680 | 0.055 | $1.812 \times 10^{-12}$ | 0.783 |
| rs6889889[A] | chr5:110458416 | TSLP | 0.352 | 1.490 | 0.068 | $5.67 \times 10^{-10}$ | 0.353 | 1.233 | 0.105 | $8.64 \times 10^{-3}$ | 1.461 | 0.058 | $4.798 \times 10^{-11}$ | 0.257 |
| rs11295611[G] | chr5:110458605 | TSLP | 0.350 | 1.502 | 0.068 | $1.95 \times 10^{-10}$ | 0.352 | 1.217 | 0.105 | 0.013 | 1.467 | 0.058 | $3.134 \times 10^{-11}$ | 0.176 |
| rs7702774[T] | chr5:110460851 | TSLP | 0.441 | 0.652 | 0.064 | $6.75 \times 10^{-10}$ | 0.434 | 0.715 | 0.101 | $3.33 \times 10^{-4}$ | 0.680 | 0.055 | $1.735 \times 10^{-12}$ | 0.781 |
| rs1043828[C] | chr5:110464008 | TSLP | 0.360 | 1.540 | 0.066 | $2.49 \times 10^{-11}$ | 0.366 | 1.225 | 0.102 | $9.72 \times 10^{-3}$ | 1.478 | 0.056 | $3.461 \times 10^{-12}$ | 0.159 |
| rs1438673[T] | chr5:110467499 | TSLP | 0.496 | 0.626 | 0.063 | $2.74 \times 10^{-12}$ | 0.490 | 0.793 | 0.099 | $3.84 \times 10^{-3}$ | 0.671 | 0.054 | $1.507 \times 10^{-13}$ | 0.193 |
| rs1438672[A] | chr5:110467753 | TSLP | 0.457 | 0.638 | 0.064 | $6.08 \times 10^{-11}$ | 0.441 | 0.780 | 0.100 | $8.36 \times 10^{-3}$ | 0.687 | 0.055 | $6.019 \times 10^{-12}$ | 0.206 |
| rs34962275[G] | chr5:110468977 | TSLP | 0.363 | 1.528 | 0.066 | $5.24 \times 10^{-11}$ | 0.368 | 1.241 | 0.102 | $8.52 \times 10^{-3}$ | 1.472 | 0.056 | $5.738 \times 10^{-12}$ | 0.185 |
| rs6594499[A] | chr5:110470137 | TSLP | 0.493 | 0.633 | 0.064 | $4.89 \times 10^{-12}$ | 0.483 | 0.779 | 0.100 | $2.48 \times 10^{-3}$ | 0.669 | 0.055 | $1.47 \times 10^{-13}$ | 0.259 |
| rs6594500[A] | chr5:110470994 | TSLP | 0.395 | 1.466 | 0.066 | $2.11 \times 10^{-9}$ | 0.410 | 1.164 | 0.102 | 0.092 | 1.392 | 0.056 | $3.399 \times 10^{-9}$ | 0.072 |
| rs12186767[G] | chr5:110471218 | TSLP | 0.358 | 1.525 | 0.067 | $3.90 \times 10^{-11}$ | 0.358 | 1.211 | 0.105 | 0.015 | 1.475 | 0.057 | $8.541 \times 10^{-12}$ | 0.141 |
| rs72784258[C] | chr5:110471615 | TSLP | 0.391 | 1.454 | 0.066 | $4.10 \times 10^{-9}$ | 0.404 | 1.197 | 0.104 | 0.048 | 1.402 | 0.057 | $2.203 \times 10^{-9}$ | 0.143 |
| rs73786772[G] | chr5:110471791 | TSLP | 0.326 | 1.455 | 0.070 | $1.06 \times 10^{-9}$ | 0.343 | 1.257 | 0.106 | $5.11 \times 10^{-3}$ | 1.478 | 0.059 | $5.004 \times 10^{-11}$ | 0.306 |
| rs55684690[T] | chr11:76057946 | c11orf30 | 0.038 | 2.109 | 0.169 | $4.20 \times 10^{-8}$ | 0.040 | 2.132 | 0.270 | $6.81 \times 10^{-5}$ | 2.637 | 0.149 | $6.961 \times 10^{-11}$ | 0.652 |
| chr11:76114003:D[T] | chr11:76114003 | c11orf30 | 0.162 | 1.637 | 0.086 | $4.56 \times 10^{-9}$ | 0.177 | 1.352 | 0.133 | $9.26 \times 10^{-3}$ | 1.578 | 0.075 | $1.007 \times 10^{-9}$ | 0.344 |
| rs12420744[G] | chr11:76114021 | c11orf30 | 0.159 | 1.620 | 0.087 | $1.27 \times 10^{-8}$ | 0.171 | 1.372 | 0.137 | $5.14 \times 10^{-3}$ | 1.585 | 0.076 | $1.232 \times 10^{-9}$ | 0.509 |
| rs1893870[T] | chr11:76117879 | c11orf30 | 0.257 | 1.451 | 0.073 | $4.34 \times 10^{-8}$ | 0.272 | 1.171 | 0.115 | 0.131 | 1.397 | 0.064 | $1.699 \times 10^{-7}$ | 0.108 |
| rs7927830[A] | chr11:76120315 | c11orf30 | 0.241 | 1.493 | 0.074 | $2.47 \times 10^{-8}$ | 0.259 | 1.126 | 0.114 | 0.240 | 1.392 | 0.065 | $3.175 \times 10^{-7}$ | 0.046 |
| rs2156708[C] | chr11:76122213 | c11orf30 | 0.241 | 1.493 | 0.075 | $2.50 \times 10^{-8}$ | 0.260 | 1.127 | 0.114 | 0.236 | 1.392 | 0.065 | $3.117 \times 10^{-7}$ | 0.047 |
| rs871911[G] | chr11:76123849 | c11orf30 | 0.235 | 1.504 | 0.076 | $9.49 \times 10^{-8}$ | 0.261 | 1.125 | 0.114 | 0.242 | 1.408 | 0.065 | $1.73 \times 10^{-7}$ | 0.034 |
| rs59382353[A] | chr11:76137243 | c11orf30 | 0.156 | 1.637 | 0.086 | $1.18 \times 10^{-8}$ | 0.168 | 1.393 | 0.136 | $4.82 \times 10^{-3}$ | 1.586 | 0.076 | $1.085 \times 10^{-9}$ | 0.514 |
| rs73004436[G] | chr11:76144139 | c11orf30 | 0.155 | 1.636 | 0.087 | $1.19 \times 10^{-8}$ | 0.167 | 1.384 | 0.136 | $5.38 \times 10^{-3}$ | 1.585 | 0.076 | $1.225 \times 10^{-9}$ | 0.495 |
| rs4426156[G] | chr11:76149594 | c11orf30 | 0.156 | 1.634 | 0.087 | $1.35 \times 10^{-8}$ | 0.167 | 1.384 | 0.136 | $5.36 \times 10^{-3}$ | 1.583 | 0.076 | $1.361 \times 10^{-9}$ | 0.503 |
| rs61894509[C] | chr11:76171935 | c11orf30 | 0.157 | 1.622 | 0.086 | $3.05 \times 10^{-8}$ | 0.167 | 1.368 | 0.136 | $7.57 \times 10^{-3}$ | 1.560 | 0.076 | $3.938 \times 10^{-9}$ | 0.495 |
| rs61969910[G] | chr11:76190383 | c11orf30 | 0.155 | 1.622 | 0.086 | $3.27 \times 10^{-8}$ | 0.167 | 1.364 | 0.136 | $8.14 \times 10^{-3}$ | 1.558 | 0.076 | $4.531 \times 10^{-9}$ | 0.484 |
| rs61894530[A] | chr11:76192036 | c11orf30 | 0.155 | 1.622 | 0.086 | $3.27 \times 10^{-8}$ | 0.167 | 1.364 | 0.136 | $8.14 \times 10^{-3}$ | 1.558 | 0.076 | $4.531 \times 10^{-9}$ | 0.484 |
| rs11532107[T] | chr11:76194993 | c11orf30 | 0.155 | 1.622 | 0.086 | $3.27 \times 10^{-8}$ | 0.167 | 1.364 | 0.136 | $8.14 \times 10^{-3}$ | 1.558 | 0.076 | $4.531 \times 10^{-9}$ | 0.484 |
| rs142931944[G] | chr11:76196566 | c11orf30 | 0.155 | 1.622 | 0.086 | $3.27 \times 10^{-8}$ | 0.167 | 1.364 | 0.136 | $8.14 \times 10^{-3}$ | 1.558 | 0.076 | $4.528 \times 10^{-9}$ | 0.484 |

TABLE 1-continued

Genome-wide significant variants: Discovery, replication and meta-analysis ORs and Pvals P values for the discovery analysis are shown in bold if directly genotyped. P values for the discovery and replication sets were generated using a missing data likelihood score test as implemented in SNPTEST2. Cutoffs, genome-wide significance ($P < 5 \times 10^{-8}$), MAF ≥ 3%, info scores ≥ 0.8. $P_{het}$, heterogeneity P value for Cochrane's Q statistic. OR, odds ratio.

| Variant [Effect Allele] | chr:pos hg19 | Gene | Discovery effect allele MAF | OR | Pval | SE | Replication effect allele MAF | OR | Pval | SE | Meta OR | SE | Pval | $P_{het}$ |
|---|---|---|---|---|---|---|---|---|---|---|---|---|---|---|
| rs11236766[A] | chr11:76208451 | c11orf30 | 0.155 | 1.618 | $4.07 \times 10^{-8}$ | 0.086 | 0.166 | 1.373 | $6.89 \times 10^{-3}$ | 0.137 | 1.558 | 0.076 | $4.564 \times 10^{-9}$ | 0.532 |
| rs61894534[T] | chr11:76210929 | c11orf30 | 0.155 | 1.618 | $4.06 \times 10^{-8}$ | 0.086 | 0.166 | 1.373 | $6.90 \times 10^{-3}$ | 0.137 | 1.558 | 0.076 | $4.554 \times 10^{-9}$ | 0.532 |
| rs11236767[A] | chr11:76211421 | c11orf30 | 0.155 | 1.618 | $4.06 \times 10^{-8}$ | 0.086 | 0.166 | 1.373 | $6.90 \times 10^{-3}$ | 0.137 | 1.558 | 0.076 | $4.557 \times 10^{-9}$ | 0.532 |
| rs57790584[C] | chr11:76212164 | c11orf30 | 0.155 | 1.618 | $4.06 \times 10^{-8}$ | 0.086 | 0.166 | 1.373 | $6.90 \times 10^{-3}$ | 0.137 | 1.558 | 0.076 | $4.557 \times 10^{-9}$ | 0.532 |
| rs7940373[T] | chr11:76216873 | c11orf30 | 0.155 | 1.618 | $4.07 \times 10^{-8}$ | 0.086 | 0.166 | 1.373 | $6.87 \times 10^{-3}$ | 0.137 | 1.558 | 0.076 | $4.542 \times 10^{-9}$ | 0.532 |
| rs61894541[G] | chr11:76231227 | c11orf30 | 0.156 | 1.616 | $4.35 \times 10^{-8}$ | 0.086 | 0.167 | 1.351 | $9.13 \times 10^{-3}$ | 0.136 | 1.550 | 0.076 | $6.522 \times 10^{-9}$ | 0.481 |
| rs1939469[G] | chr11:76236220 | c11orf30 | 0.156 | 1.617 | $3.98 \times 10^{-8}$ | 0.086 | 0.167 | 1.360 | $8.38 \times 10^{-3}$ | 0.136 | 1.553 | 0.075 | $5.512 \times 10^{-9}$ | 0.492 |
| rs11236775[A] | chr11:76239148 | c11orf30 | 0.156 | 1.615 | $4.93 \times 10^{-8}$ | 0.086 | 0.166 | 1.362 | $6.90 \times 10^{-3}$ | 0.137 | 1.556 | 0.076 | $5.354 \times 10^{-9}$ | 0.550 |
| rs61894547[T] | chr11:76248630 | c11orf30 | 0.043 | 2.210 | $2.01 \times 10^{-9}$ | 0.155 | 0.048 | 1.818 | $7.49 \times 10^{-4}$ | 0.238 | 2.439 | 0.135 | $3.643 \times 10^{-11}$ | 0.661 |
| chr11:76251777:D[T] | chr11:76251777 | c11orf30 | 0.156 | 1.617 | $3.41 \times 10^{-8}$ | 0.086 | 0.166 | 1.350 | $8.05 \times 10^{-3}$ | 0.137 | 1.560 | 0.076 | $4.585 \times 10^{-9}$ | 0.499 |
| rs3758716[T] | chr11:76254529 | c11orf30 | 0.156 | 1.617 | $3.33 \times 10^{-8}$ | 0.086 | 0.166 | 1.349 | $8.24 \times 10^{-3}$ | 0.137 | 1.560 | 0.076 | $4.604 \times 10^{-9}$ | 0.493 |
| rs3758715[T] | chr11:76254539 | c11orf30 | 0.156 | 1.617 | $3.33 \times 10^{-8}$ | 0.086 | 0.166 | 1.349 | $8.24 \times 10^{-3}$ | 0.137 | 1.560 | 0.076 | $4.608 \times 10^{-9}$ | 0.493 |
| rs17134961[C] | chr11:76257759 | c11orf30 | 0.156 | 1.611 | $3.49 \times 10^{-8}$ | 0.087 | 0.166 | 1.343 | $9.62 \times 10^{-3}$ | 0.136 | 1.556 | 0.076 | $5.746 \times 10^{-9}$ | 0.456 |
| rs2155221[T] | chr11:76266267 | c11orf30 | 0.156 | 1.604 | $4.44 \times 10^{-8}$ | 0.087 | 0.166 | 1.338 | 0.010 | 0.137 | 1.552 | 0.076 | $7.621 \times 10^{-9}$ | 0.461 |
| rs55646091[A] | chr11:76299431 | c11orf30 | 0.044 | 2.219 | $5.38 \times 10^{-10}$ | 0.157 | 0.050 | 1.584 | $4.33 \times 10^{-3}$ | 0.237 | 2.414 | 0.135 | $7.672 \times 10^{-11}$ | 0.315 |
| rs167769[T] | chr12:57503775 | STAT6 | 0.377 | 1.498 | $2.29 \times 10^{-8}$ | 0.066 | 0.367 | 1.123 | 0.209 | 0.105 | 1.351 | 0.058 | $2.199 \times 10^{-7}$ | 0.064 |
| rs73120411[T] | chr12:57519826 | STAT6 | 0.345 | 1.475 | $2.59 \times 10^{-8}$ | 0.069 | 0.341 | 1.080 | 0.245 | 0.111 | 1.368 | 0.061 | $3.089 \times 10^{-7}$ | 0.056 |
| rs3815700[C] | chr9:33093252 | ANKRD27 | 0.140 | 1.653 | $4.54 \times 10^{-12}$ | 0.092 | 0.144 | 1.098 | 0.413 | 0.144 | 1.618 | 0.081 | $2.366 \times 10^{-9}$ | 0.003 |
| rs10410895[G] | chr9:33093655 | ANKRD27 | 0.140 | 1.474 | $2.27 \times 10^{-8}$ | 0.096 | 0.148 | 1.066 | 0.522 | 0.144 | 1.485 | 0.083 | $1.847 \times 10^{-6}$ | 0.012 |
| rs8008716[G] | chr14:27125765 | NOVA1 | 0.087 | 1.455 | $2.07 \times 10^{-6}$ | 0.117 | 0.092 | 1.579 | 0.002 | 0.164 | 1.712 | 0.100 | $6.93 \times 10^{-8}$ | 0.793 |

TABLE 2

Conditional analyses at the c11orf30 and STAT6 loci on EoE comorbidity status. P values were generated using a missing data likelihood score test as implemented in SNPTEST2 with and without conditioning on comorbidities.

| Variant [Effect Allele] | chr:pos hg19 | Gene | MAF | effect allele Not conditioning on comorbidities | | | Conditional analysis | | |
|---|---|---|---|---|---|---|---|---|---|
| | | | | OR | Pval | SE | OR | Pval | SE |
| rs55684690[T] | chr11:76057946 | c11orf30 | 0.038 | 2.305 | $4.85 \times 10^{-6}$ | 0.250 | 2.128 | $1.88 \times 10^{-4}$ | 0.339 |
| chr11:76114003:D[T] | chr11:76114003 | c11orf30 | 0.162 | 1.709 | $2.98 \times 10^{-7}$ | 0.127 | 1.791 | $1.51 \times 10^{-3}$ | 0.162 |
| rs12420744[G] | chr11:76114021 | c11orf30 | 0.159 | 1.719 | $2.50 \times 10^{-7}$ | 0.128 | 1.781 | $1.39 \times 10^{-3}$ | 0.163 |
| rs1893870[T] | chr11:76117879 | c11orf30 | 0.258 | 1.532 | $1.52 \times 10^{-5}$ | 0.106 | 1.510 | $6.82 \times 10^{-3}$ | 0.137 |
| rs7927830[A] | chr11:76120315 | c11orf30 | 0.240 | 1.535 | $1.78 \times 10^{-5}$ | 0.109 | 1.596 | $4.47 \times 10^{-3}$ | 0.140 |
| rs2156708[C] | chr11:76122213 | c11orf30 | 0.241 | 1.534 | $1.83 \times 10^{-5}$ | 0.109 | 1.595 | $4.58 \times 10^{-3}$ | 0.140 |
| rs871911[G] | chr11:76123849 | c11orf30 | 0.235 | 1.520 | $2.27 \times 10^{-5}$ | 0.111 | 1.595 | $5.04 \times 10^{-3}$ | 0.142 |
| rs59382353[A] | chr11:76137243 | c11orf30 | 0.157 | 1.753 | $1.37 \times 10^{-7}$ | 0.128 | 1.854 | $1.80 \times 10^{-4}$ | 0.160 |
| rs73004436[G] | chr11:76144139 | c11orf30 | 0.157 | 1.747 | $1.44 \times 10^{-7}$ | 0.128 | 1.852 | $1.68 \times 10^{-4}$ | 0.160 |
| rs4426156[G] | chr11:76149594 | c11orf30 | 0.157 | 1.745 | $1.54 \times 10^{-7}$ | 0.128 | 1.850 | $1.70 \times 10^{-4}$ | 0.160 |
| rs61894509[C] | chr11:76171935 | c11orf30 | 0.158 | 1.733 | $2.12 \times 10^{-7}$ | 0.128 | 1.823 | $3.58 \times 10^{-4}$ | 0.160 |
| rs61696910[G] | chr11:76190383 | c11orf30 | 0.157 | 1.725 | $2.96 \times 10^{-7}$ | 0.128 | 1.815 | $2.98 \times 10^{-4}$ | 0.160 |
| rs61894530[A] | chr11:76192036 | c11orf30 | 0.157 | 1.725 | $2.96 \times 10^{-7}$ | 0.128 | 1.815 | $2.98 \times 10^{-4}$ | 0.160 |
| rs11532107[T] | chr11:76194993 | c11orf30 | 0.157 | 1.725 | $2.96 \times 10^{-7}$ | 0.128 | 1.815 | $2.98 \times 10^{-4}$ | 0.160 |
| rs142931944[G] | chr11:76196566 | c11orf30 | 0.157 | 1.725 | $2.96 \times 10^{-7}$ | 0.128 | 1.815 | $2.98 \times 10^{-4}$ | 0.160 |
| rs11236766[A] | chr11:76208451 | c11orf30 | 0.157 | 1.721 | $2.90 \times 10^{-7}$ | 0.128 | 1.813 | $2.99 \times 10^{-4}$ | 0.160 |
| rs61894534[T] | chr11:76210929 | c11orf30 | 0.157 | 1.721 | $2.89 \times 10^{-7}$ | 0.128 | 1.813 | $2.98 \times 10^{-4}$ | 0.160 |
| rs11236767[A] | chr11:76211421 | c11orf30 | 0.157 | 1.721 | $2.89 \times 10^{-7}$ | 0.128 | 1.813 | $2.98 \times 10^{-4}$ | 0.160 |
| rs57790584[C] | chr11:76212164 | c11orf30 | 0.157 | 1.721 | $2.89 \times 10^{-7}$ | 0.128 | 1.813 | $2.98 \times 10^{-4}$ | 0.160 |
| rs7940373[T] | chr11:76216873 | c11orf30 | 0.157 | 1.721 | $2.89 \times 10^{-7}$ | 0.128 | 1.813 | $2.98 \times 10^{-4}$ | 0.160 |
| rs61894541[G] | chr11:76231227 | c11orf30 | 0.157 | 1.728 | $2.14 \times 10^{-7}$ | 0.128 | 1.808 | $3.23 \times 10^{-4}$ | 0.160 |
| rs1939469[G] | chr11:76236220 | c11orf30 | 0.157 | 1.727 | $2.23 \times 10^{-7}$ | 0.128 | 1.807 | $3.26 \times 10^{-4}$ | 0.160 |
| rs11236775[A] | chr11:76239148 | c11orf30 | 0.157 | 1.717 | $3.11 \times 10^{-7}$ | 0.128 | 1.810 | $3.08 \times 10^{-4}$ | 0.160 |
| rs61894547[T] | chr11:76248630 | c11orf30 | 0.043 | 2.202 | $3.20 \times 10^{-6}$ | 0.237 | 2.288 | $3.27 \times 10^{-3}$ | 0.301 |
| chr11:76251777:D[T] | chr11:76251777 | c11orf30 | 0.157 | 1.718 | $2.95 \times 10^{-7}$ | 0.128 | 1.809 | $2.84 \times 10^{-4}$ | 0.160 |
| rs3758716[T] | chr11:76254529 | c11orf30 | 0.158 | 1.717 | $3.05 \times 10^{-7}$ | 0.128 | 1.809 | $2.83 \times 10^{-4}$ | 0.160 |
| rs3758715[T] | chr11:76254539 | c11orf30 | 0.158 | 1.717 | $3.05 \times 10^{-7}$ | 0.128 | 1.809 | $2.83 \times 10^{-4}$ | 0.160 |
| rs17134961[C] | chr11:76257759 | c11orf30 | 0.157 | 1.729 | $1.97 \times 10^{-7}$ | 0.128 | 1.779 | $5.56 \times 10^{-4}$ | 0.161 |
| rs2155221[T] | chr11:76266267 | c11orf30 | 0.158 | 1.721 | $2.37 \times 10^{-7}$ | 0.128 | 1.777 | $5.46 \times 10^{-4}$ | 0.161 |
| rs55646091[A] | chr11:76299431 | c11orf30 | 0.044 | 2.138 | $9.32 \times 10^{-7}$ | 0.240 | 2.344 | $1.97 \times 10^{-3}$ | 0.299 |
| rs167769[T] | chr12:57503775 | STAT6 | 0.377 | 1.455 | $7.72 \times 10^{-5}$ | 0.096 | 1.680 | 0.01 | 0.154 |
| rs73120411[T] | chr12:57519826 | STAT6 | 0.346 | 1.469 | $4.02 \times 10^{-5}$ | 0.101 | 1.669 | $5.37 \times 10^{-3}$ | 0.163 |

TABLE 3

P-values following conditional analysis on rs55646091 and rs11236791 in the discovery cohort. Variants that show significant increase in P-value following the conditional analyses are shown in bold type. P values were generated using a missing data likelihood score test as implemented in SNPTEST2.

| c11orf30 | | | Discovery | Conditional analyses | |
|---|---|---|---|---|---|
| chromosome | pos | all_maf | Pval | Pval-cond-rs55646091 | Pval-cond-rs11236791 |
| rs55684690[T] | 76057946 | 0.028 | $4.23 \times 10-8$ | 0.0402196 | $3.56E-10$ |
| rs61894547[T] | 76248630 | 0.032 | $2.01 \times 10-9$ | 0.425467 | $1.81 \times 10-9$ |
| rs2212434[T] | 76281593 | 0.413 | $9.14 \times 10-7$ | $2.31 \times 10-8$ | 0.636761 |
| rs61893460[A] | 76291154 | 0.418 | $1.26 \times 10-6$ | $3.36 \times 10-8$ | 0.186305 |
| rs7126418[T] | 76292573 | 0.419 | $1.27 \times 10-6$ | $5.43 \times 10-8$ | 0.0682383 |
| rs7110818[T] | 76292575 | 0.419 | $1.27 \times 10-6$ | $5.43 \times 10-8$ | 0.0682379 |
| rs7114362[T] | 76293070 | 0.455 | $3.73 \times 10-5$ | $1.37 \times 10-7$ | 0.769806 |
| rs7936070[T] | 76293527 | 0.409 | $4.07 \times 10-6$ | $5.93 \times 10-6$ | 0.873197 |
| rs7936312[T] | 76293726 | 0.461 | $7.15 \times 10-6$ | $9.65 \times 10-7$ | 0.218637 |
| rs7936323[A] | 76293758 | 0.449 | $3.68 \times 10-6$ | $2.25 \times 10-7$ | 0.373308 |
| rs4494327[T] | 76294836 | 0.480 | $2.79 \times 10-6$ | 0.00945432 | $6.83 \times 10-4$ |
| rs11236791[A] | 76295598 | 0.406 | $1.60 \times 10-6$ | $1.90 \times 10-9$ | 0.999358 |
| rs10160518[G] | 76296671 | 0.466 | $2.21 \times 10-6$ | 0.0403663 | $3.79 \times 10-5$ |
| chr11:76298625:I[GT] | 76298625 | 0.405 | $1.56 \times 10-6$ | $1.22 \times 10-9$ | 0.395477 |
| rs2155219[T] | 76299194 | 0.467 | $1.30 \times 10-6$ | 0.0242987 | $1.28 \times 10-4$ |
| rs55646091[A] | 76299431 | 0.033 | $5.38 \times 10-10$ | 0.999701 | $2.19 \times 10-9$ |
| rs11236797[A] | 76299649 | 0.407 | $1.58 \times 10-6$ | $2.51 \times 10-9$ | 0.81221 |
| chr11:76299844:D[C] | 76299844 | 0.469 | $1.52 \times 10-6$ | 0.0277185 | $1.33 \times 10-4$ |
| rs7930763[A] | 76302073 | 0.466 | $1.65 \times 10-6$ | 0.0294863 | $1.28 \times 10-4$ |

TABLE 4

Transcriptome sequencing of genes under the GWAS peaks
from eosphageal epithelium of EoE cases and controls.

| Gene | Chr | FPKM case | FPKM control | Log2 (fold change) | Pval |
|---|---|---|---|---|---|
| CAPN14 | 2 | 9.828 | 0.631 | 3.962 | $5.00 \times 10^{-5}$ |
| GALNT14 | 2 | 14.391 | 13.102 | 0.135 | 0.604 |
| TSLP | 5 | 2.232 | 1.755 | 0.347 | 0.525 |
| WDR36 | 5 | 7.398 | 8.403 | −0.184 | 0.439 |
| c11orf30 | 11 | 1.790 | 1.926 | −0.106 | 0.860 |
| LRRC32 | 11 | 0.125 | 0.040 | 1.6391 | 1 |
| STAT6 | 12 | 48.3 | 45.6 | 0.08 | 0.737 |
| ANKRD27 | 19 | 12.38 | 12.23 | 0.018 | 0.939 |
| NOVA1 | 14 | 0.58 | 0.94 | −0.698 | 0.610 |

FPKM, Fragments Per Kilobase of transcript per Million mapped reads.
P values calculated from a negative binomial model estimated from data to obtain variance estimates.
Log2 fold change, change in the expression level between cases and controls.

TABLE 5

Pathway analysis of differentially expressed genes from the transcriptome sequencing of EoE and control esophageal epithelial cells.

| Direction | Category | Term | Gene count | P-value | Benjamini |
|---|---|---|---|---|---|
| ↑ | GOTERM_BP_FAT | epidermis development | 23 | $9.80 \times 10^{-12}$ | $1.50 \times 10^{-8}$ |
| ↑ | GOTERM_BP_FAT | ectoderm development | 23 | $4.70 \times 10^{-11}$ | $3.60 \times 10^{-8}$ |
| ↑ | SP_PIR_KEYWORDS | glycoprotein | 126 | $3.10 \times 10^{-10}$ | $1.20 \times 10^{-7}$ |
| ↑ | SP_PIR_KEYWORDS | signal | 103 | $4.10 \times 10^{-10}$ | $7.60 \times 10^{-8}$ |
| ↑ | GOTERM_BP_FAT | epithelial cell differentiation | 16 | $7.10 \times 10^{-8}$ | $3.60 \times 10^{-5}$ |
| ↑ | SP_PIR_KEYWORDS | protease inhibitor | 13 | $3.50 \times 10^{-7}$ | $4.30 \times 10^{-5}$ |
| ↑ | GOTERM_BP_FAT | epidermal cell differentiation | 11 | $1.20 \times 10^{-6}$ | $4.80 \times 10^{-4}$ |
| ↑ | SP_PIR_KEYWORDS | Serine protease inhibitor | 11 | $1.20 \times 10^{-6}$ | $1.10 \times 10^{-4}$ |
| ↑ | GOTERM_MF_FAT | serine-type endopeptidase inhibitor activity | 12 | $1.30 \times 10^{-6}$ | $6.00 \times 10^{-4}$ |
| ↑ | GOTERM_BP_FAT | epithelium development | 18 | $2.30 \times 10^{-6}$ | $6.90 \times 10^{-4}$ |
| ↑ | GOTERM_CC_FAT | cornified envelope | 7 | $2.70 \times 10^{-6}$ | $7.00 \times 10^{-4}$ |
| ↑ | GOTERM_MF_FAT | endopeptidase inhibitor activity | 14 | $3.70 \times 10^{-6}$ | $8.90 \times 10^{-4}$ |
| ↑ | GOTERM_BP_FAT | keratinocyte differentiation | 10 | $5.00 \times 10^{-6}$ | $1.30 \times 10^{-3}$ |
| ↑ | GOTERM_MF_FAT | peptidase inhibitor activity | 14 | $6.70 \times 10^{-6}$ | $1.10 \times 10^{-3}$ |
| ↑ | GOTERM_BP_FAT | peptide cross-linking | 7 | $8.70 \times 10^{-6}$ | $1.90 \times 10^{-3}$ |
| ↑ | SP_PIR_KEYWORDS | Secreted | 54 | $1.70 \times 10^{-5}$ | $1.30 \times 10^{-3}$ |
| ↑ | SP_PIR_KEYWORDS | polymorphism | 238 | $1.80 \times 10^{-5}$ | $1.10 \times 10^{-3}$ |
| ↑ | GOTERM_CC_FAT | apical plasma membrane | 12 | $4.90 \times 10^{-5}$ | $6.50 \times 10^{-3}$ |
| ↑ | GOTERM_MF_FAT | enzyme inhibitor activity | 17 | $5.70 \times 10^{-5}$ | $6.90 \times 10^{-3}$ |
| ↑ | SP_PIR_KEYWORDS | disulfide bond | 78 | $8.80 \times 10^{-5}$ | $4.60 \times 10^{-3}$ |
| ↑ | SP_PIR_KEYWORDS | Ichthyosis | 6 | $1.50 \times 10^{-4}$ | $7.00 \times 10^{-3}$ |
| ↑ | GOTERM_CC_FAT | apical part of cell | 13 | $1.70 \times 10^{-4}$ | $1.50 \times 10^{-2}$ |
| ↑ | GOTERM_CC_FAT | extracellular region | 61 | $2.20 \times 10^{-4}$ | $1.40 \times 10^{-2}$ |
| ↑ | GOTERM_MF_FAT | protein binding, bridging | 9 | $4.10 \times 10^{-4}$ | $3.80 \times 10^{-2}$ |
| ↑ | GOTERM_MF_FAT | structural molecule activity | 26 | $4.30 \times 10^{-4}$ | $3.40 \times 10^{-2}$ |
| ↑ | GOTERM_CC_FAT | plasma membrane part | 64 | $4.80 \times 10^{-4}$ | $2.50 \times 10^{-2}$ |
| ↑ | SP_PIR_KEYWORDS | keratinization | 6 | $6.10 \times 10^{-4}$ | $2.50 \times 10^{-2}$ |
| ↑ | GOTERM_MF_FAT | serine-type endopeptidase activity | 11 | $7.00 \times 10^{-4}$ | $4.70 \times 10^{-2}$ |
| ↑ | SP_PIR_KEYWORDS | ectodermal dysplasia | 5 | $7.20 \times 10^{-4}$ | $2.60 \times 10^{-2}$ |
| ↑ | SP_PIR_KEYWORDS | membrane | 137 | $9.20 \times 10^{-4}$ | $3.00 \times 10^{-2}$ |
| ↑ | GOTERM_CC_FAT | plasma membrane | 96 | $1.10 \times 10^{-3}$ | $4.80 \times 10^{-2}$ |
| ↑ | SP_PIR_KEYWORDS | cell adhesion | 18 | $1.20 \times 10^{-3}$ | $3.60 \times 10^{-2}$ |
| ↑ | SP_PIR_KEYWORDS | disease mutation | 45 | $1.40 \times 10^{-3}$ | $4.00 \times 10^{-2}$ |
| ↑ | SP_PIR_KEYWORDS | calcium | 27 | $1.80 \times 10^{-3}$ | $4.60 \times 10^{-2}$ |
| ↓ | GOTERM_BP_FAT | M phase | 34 | $2.30 \times 10^{-26}$ | $2.80 \times 10^{-23}$ |
| ↓ | GOTERM_BP_FAT | cell cycle phase | 36 | $1.90 \times 10^{-25}$ | $1.10 \times 10^{-22}$ |
| ↓ | GOTERM_BP_FAT | nuclear division | 29 | $3.10 \times 10^{-25}$ | $1.20 \times 10^{-22}$ |
| ↓ | GOTERM_BP_FAT | mitosis | 29 | $3.10 \times 10^{-25}$ | $1.20 \times 10^{-22}$ |

TABLE 5-continued

Pathway analysis of differentially expressed genes from the transcriptome sequencing of EoE and control esophageal epithelial cells.

| Direction | Category | Term | Gene count | P-value | Benjamini |
|---|---|---|---|---|---|
| ↓ | GOTERM_BP_FAT | M phase of mitotic cell cycle | 29 | $5.10 \times 10^{-25}$ | $1.50 \times 10^{-22}$ |
| ↓ | GOTERM_BP_FAT | organelle fission | 29 | $9.60 \times 10^{-25}$ | $2.30 \times 10^{-22}$ |
| ↓ | GOTERM_BP_FAT | mitotic cell cycle | 34 | $1.00 \times 10^{-24}$ | $2.10 \times 10^{-22}$ |
| ↓ | SP_PIR_KEYWORDS | mitosis | 25 | $1.10 \times 10^{-23}$ | $2.40 \times 10^{-21}$ |
| ↓ | GOTERM_BP_FAT | cell cycle process | 37 | $5.40 \times 10^{-22}$ | $9.20 \times 10^{-20}$ |
| ↓ | SP_PIR_KEYWORDS | cell cycle | 32 | $1.30 \times 10^{-21}$ | $1.50 \times 10^{-19}$ |
| ↓ | SP_PIR_KEYWORDS | cell division | 26 | $4.20 \times 10^{-21}$ | $3.10 \times 10^{-19}$ |
| ↓ | GOTERM_BP_FAT | cell cycle | 40 | $3.30 \times 10^{-20}$ | $4.90 \times 10^{-18}$ |
| ↓ | GOTERM_CC_FAT | spindle | 21 | $6.30 \times 10^{-19}$ | $1.10 \times 10^{-16}$ |
| ↓ | GOTERM_BP_FAT | cell division | 24 | $5.40 \times 10^{-16}$ | $7.40 \times 10^{-14}$ |
| ↓ | GOTERM_CC_FAT | microtubule cytoskeleton | 29 | $8.50 \times 10^{-15}$ | $7.50 \times 10^{-13}$ |
| ↓ | GOTERM_CC_FAT | chromosome, centromeric region | 16 | $1.30 \times 10^{-13}$ | $7.50 \times 10^{-12}$ |
| ↓ | GOTERM_CC_FAT | cytoskeletal part | 34 | $1.30 \times 10^{-12}$ | $5.60 \times 10^{-11}$ |
| ↓ | GOTERM_CC_FAT | condensed chromosome, centromeric region | 12 | $7.50 \times 10^{-12}$ | $2.70 \times 10^{-10}$ |
| ↓ | GOTERM_BP_FAT | microtubule-based process | 18 | $5.50 \times 10^{-11}$ | $6.60 \times 10^{-9}$ |
| ↓ | GOTERM_CC_FAT | condensed chromosome | 14 | $6.30 \times 10^{-11}$ | $1.90 \times 10^{-9}$ |
| ↓ | GOTERM_BP_FAT | chromosome segregation | 12 | $9.20 \times 10^{-11}$ | $1.00 \times 10^{-8}$ |
| ↓ | SP_PIR_KEYWORDS | cytoskeleton | 24 | $1.50 \times 10^{-10}$ | $8.70 \times 10^{-9}$ |
| ↓ | SP_PIR_KEYWORDS | centromere | 9 | $2.30 \times 10^{-10}$ | $1.10 \times 10^{-8}$ |
| ↓ | SP_PIR_KEYWORDS | kinetochore | 10 | $6.60 \times 10^{-10}$ | $2.50 \times 10^{-8}$ |
| ↓ | GOTERM_CC_FAT | condensed chromosome kinetochore | 10 | $1.30 \times 10^{-9}$ | $3.30 \times 10^{-8}$ |
| ↓ | GOTERM_CC_FAT | cytoskeleton | 36 | $1.40 \times 10^{-9}$ | $3.20 \times 10^{-8}$ |
| ↓ | GOTERM_CC_FAT | kinetochore | 10 | $1.70 \times 10^{-8}$ | $3.40 \times 10^{-7}$ |
| ↓ | GOTERM_BP_FAT | regulation of cell cycle | 17 | $2.50 \times 10^{-8}$ | $2.50 \times 10^{-6}$ |
| ↓ | SP_PIR_KEYWORDS | phosphoprotein | 85 | $2.90 \times 10^{-8}$ | $9.40 \times 10^{-7}$ |
| ↓ | GOTERM_BP_FAT | spindle organization | 8 | $1.00 \times 10^{-7}$ | $9.60 \times 10^{-6}$ |
| ↓ | GOTERM_CC_FAT | chromosomal part | 17 | $1.60 \times 10^{-7}$ | $2.90 \times 10^{-6}$ |
| ↓ | GOTERM_CC_FAT | chromosome | 18 | $3.30 \times 10^{-7}$ | $5.30 \times 10^{-6}$ |
| ↓ | GOTERM_BP_FAT | microtubule cytoskeleton organization | 11 | $5.60 \times 10^{-7}$ | $4.80 \times 10^{-5}$ |
| ↓ | GOTERM_BP_FAT | regulation of mitotic cell cycle | 11 | $7.60 \times 10^{-7}$ | $6.10 \times 10^{-5}$ |
| ↓ | GOTERM_BP_FAT | cytoskeleton organization | 17 | $1.00 \times 10^{-6}$ | $7.80 \times 10^{-5}$ |
| ↓ | GOTERM_CC_FAT | non-membrane-bounded organelle | 45 | $1.20 \times 10^{-6}$ | $1.80 \times 10^{-5}$ |
| ↓ | GOTERM_CC_FAT | intracellular non-membrane-bounded organelle | 45 | $1.20 \times 10^{-6}$ | $1.80 \times 10^{-5}$ |
| ↓ | GOTERM_BP_FAT | organelle localization | 9 | $1.30 \times 10^{-6}$ | $8.80 \times 10^{-5}$ |
| ↓ | SP_PIR_KEYWORDS | cytoplasm | 48 | $1.50 \times 10^{-6}$ | $4.10 \times 10^{-5}$ |
| ↓ | GOTERM_BP_FAT | mitotic cell cycle checkpoint | 7 | $1.70 \times 10^{-6}$ | $1.20 \times 10^{-4}$ |
| ↓ | GOTERM_MF_FAT | microtubule motor activity | 8 | $2.30 \times 10^{-6}$ | $6.10 \times 10^{-4}$ |
| ↓ | GOTERM_BP_FAT | spindle checkpoint | 5 | $2.50 \times 10^{-6}$ | $1.60 \times 10^{-4}$ |
| ↓ | GOTERM_CC_FAT | microtubule | 13 | $3.70 \times 10^{-6}$ | $5.00 \times 10^{-5}$ |
| ↓ | GOTERM_CC_FAT | spindle microtubule | 6 | $4.10 \times 10^{-6}$ | $5.30 \times 10^{-5}$ |
| ↓ | GOTERM_BP_FAT | microtubule-based movement | 9 | $5.90 \times 10^{-6}$ | $3.50 \times 10^{-4}$ |
| ↓ | GOTERM_BP_FAT | regulation of cell cycle process | 9 | $6.30 \times 10^{-6}$ | $3.60 \times 10^{-4}$ |
| ↓ | SP_PIR_KEYWORDS | microtubule | 11 | $6.60 \times 10^{-6}$ | $1.70 \times 10^{-4}$ |
| ↓ | GOTERM_BP_FAT | establishment of chromosome localization | 5 | $6.70 \times 10^{-6}$ | $3.70 \times 10^{-4}$ |
| ↓ | GOTERM_BP_FAT | chromosome localization | 5 | $6.70 \times 10^{-6}$ | $3.70 \times 10^{-4}$ |
| ↓ | GOTERM_CC_FAT | spindle pole | 6 | $9.40 \times 10^{-6}$ | $1.10 \times 10^{-4}$ |
| ↓ | GOTERM_BP_FAT | cell cycle checkpoint | 8 | $1.30 \times 10^{-5}$ | $7.00 \times 10^{-4}$ |
| ↓ | GOTERM_CC_FAT | midbody | 5 | $1.40 \times 10^{-5}$ | $1.60 \times 10^{-4}$ |

TABLE 5-continued

Pathway analysis of differentially expressed genes from the transcriptome sequencing of EoE and control esophageal epithelial cells.

| Direction | Category | Term | Gene count | P-value | Benjamini |
|---|---|---|---|---|---|
| ↓ | GOTERM_BP_FAT | mitotic sister chromatid segregation | 6 | $1.40 \times 10^{-5}$ | $6.80 \times 10^{-4}$ |
| ↓ | GOTERM_BP_FAT | sister chromatid segregation | 6 | $1.60 \times 10^{-5}$ | $7.40 \times 10^{-4}$ |
| ↓ | GOTERM_BP_FAT | establishment of organelle localization | 7 | $2.80 \times 10^{-5}$ | $1.30 \times 10^{-3}$ |
| ↓ | GOTERM_BP_FAT | regulation of mitotic metaphase/anaphase transition | 5 | $3.40 \times 10^{-5}$ | $1.50 \times 10^{-3}$ |
| ↓ | SP_PIR_KEYWORDS | motor protein | 8 | $4.70 \times 10^{-5}$ | $1.10 \times 10^{-3}$ |
| ↓ | GOTERM_CC_FAT | outer kinetochore of condensed chromosome | 4 | $4.90 \times 10^{-5}$ | $5.10 \times 10^{-4}$ |
| ↓ | GOTERM_CC_FAT | microtubule organizing center | 11 | $5.90 \times 10^{-5}$ | $5.80 \times 10^{-4}$ |
| ↓ | SP_PIR_KEYWORDS | Chromosome partition | 5 | $6.90 \times 10^{-5}$ | $1.40 \times 10^{-3}$ |
| ↓ | SP_PIR_KEYWORDS | chromosomal protein | 8 | $8.50 \times 10^{-5}$ | $1.60 \times 10^{-3}$ |
| ↓ | SP_PIR_KEYWORDS | ubl conjugation | 15 | $8.70 \times 10^{-5}$ | $1.50 \times 10^{-3}$ |
| ↓ | GOTERM_BP_FAT | negative regulation of mitotic metaphase/anaphase transition | 4 | $9.90 \times 10^{-5}$ | $4.20 \times 10^{-3}$ |
| ↓ | GOTERM_BP_FAT | mitotic cell cycle spindle assembly checkpoint | 4 | $9.90 \times 10^{-5}$ | $4.20 \times 10^{-3}$ |
| ↓ | GOTERM_BP_FAT | cell proliferation | 14 | $1.00 \times 10^{-4}$ | $4.10 \times 10^{-3}$ |
| ↓ | GOTERM_CC_FAT | centrosome | 10 | $1.20 \times 10^{-4}$ | $1.20 \times 10^{-3}$ |
| ↓ | GOTERM_BP_FAT | negative regulation of mitosis | 4 | $1.30 \times 10^{-4}$ | $5.20 \times 10^{-3}$ |
| ↓ | GOTERM_BP_FAT | negative regulation of nuclear division | 4 | $1.30 \times 10^{-4}$ | $5.20 \times 10^{-3}$ |
| ↓ | GOTERM_MF_FAT | motor activity | 8 | $1.30 \times 10^{-4}$ | $1.70 \times 10^{-2}$ |
| ↓ | GOTERM_CC_FAT | chromosome passenger complex | 3 | $2.10 \times 10^{-4}$ | $1.90 \times 10^{-3}$ |
| ↓ | GOTERM_CC_FAT | microtubule associated complex | 7 | $2.30 \times 10^{-4}$ | $2.00 \times 10^{-3}$ |
| ↓ | GOTERM_BP_FAT | mitotic spindle organization | 4 | $2.70 \times 10^{-4}$ | $1.00 \times 10^{-2}$ |
| ↓ | SP_PIR_KEYWORDS | extracellular matrix | 9 | $3.50 \times 10^{-4}$ | $5.70 \times 10^{-3}$ |
| ↓ | SP_PIR_KEYWORDS | polymorphism | 103 | $4.30 \times 10^{-4}$ | $6.50 \times 10^{-3}$ |
| ↓ | GOTERM_BP_FAT | negative regulation of organelle organization | 6 | $7.10 \times 10^{-4}$ | $2.60 \times 10^{-2}$ |
| ↓ | SP_PIR_KEYWORDS | metalloprotease | 7 | $7.80 \times 10^{-4}$ | $1.10 \times 10^{-2}$ |
| ↓ | GOTERM_BP_FAT | phosphoinositide-mediated signaling | 6 | $9.80 \times 10^{-4}$ | $3.50 \times 10^{-2}$ |
| ↓ | GOTERM_BP_FAT | centromere complex assembly | 3 | $1.10 \times 10^{-3}$ | $3.80 \times 10^{-2}$ |
| ↓ | SP_PIR_KEYWORDS | heparin-binding | 5 | $1.20 \times 10^{-3}$ | $1.60 \times 10^{-2}$ |
| ↓ | GOTERM_BP_FAT | negative regulation of cell cycle process | 4 | $1.30 \times 10^{-3}$ | $4.20 \times 10^{-2}$ |
| ↓ | GOTERM_BP_FAT | regulation of mitosis | 5 | $1.40 \times 10^{-3}$ | $4.50 \times 10^{-2}$ |
| ↓ | GOTERM_BP_FAT | regulation of nuclear division | 5 | $1.40 \times 10^{-3}$ | $4.50 \times 10^{-2}$ |
| ↓ | GOTERM_BP_FAT | G2 phase of mitotic cell cycle | 3 | $1.50 \times 10^{-3}$ | $4.80 \times 10^{-2}$ |
| ↓ | GOTERM_BP_FAT | G2 phase | 3 | $1.50 \times 10^{-3}$ | $4.80 \times 10^{-2}$ |

Direction: indicates whether the term was enriched in genes whose expression was increased in cases vs controls (↑) or decreased in cases vs controls (↓).
Category: GOTERM is a GO Biological process terms and SP_PIR refers to Protein Information Resource (PIR) Keywords.
Gene count: number of genes in the differentially expressed list that mapped to the term.
Benjamini: FDR corrected P-value.
P values derived from a Fisher-exact test of the target gene list compared to the genome background

What is claimed is:

1. A method for treating eosinophilic esophagitis (EoE) in a human subject in need thereof, the method comprising:
    (a) obtaining a biological sample from the subject;
    (b) detecting in the sample the presence of at least one EoE associated single nucleotide polymorphisms (SNP) in a target nucleic acid in said sample, wherein said SNP is present in a gene sequence from ANKDR27, said SNPs being selected from a C allele at rs3815700 in ANKRD27, and a G allele at rs10410895 in ANKRD27 and; and
    (c) administering to the subject an agent that ameliorates EoE symptoms.

2. The method of claim 1, wherein detecting the presence of said at least one EoE associated SNP comprises performing a process selected from specific hybridization, measurement of allele size, restriction fragment length polymorphism analysis, allele specific hybridization analysis, single base primer extension reaction, and sequencing of an amplified polynucleotide.

3. The method of claim 1, wherein the target nucleic acid is DNA.

4. The method of claim 1, wherein the target sequence is a ribonucleic acid (RNA).

5. The method of claim 1, wherein the nucleic acids are obtained from an isolated cell of the human subject.

6. The method of claim 1, further comprising detecting at least one of an EoE associated SNP in a gene sequence from CAPN14, selected from
    a G allele at rs78464756,
    a G allele at rs74732520,
    an A allele at rs143457388, and
    an A allele at rs149864795.

7. The method of claim 1, further comprising detecting at least one of an EoE associated SNP selected from
    a T allele at rs55684690 in c11orf30,
    a T allele at rs55684690 in c11orf30,
    a G allele at rs12420744 in c11orf30,
    a T allele at rs1893870 in c11orf30,
    an A allele at rs7927830 in c11orf30,
    a C allele at rs2156708 in c11orf30,
    a G allele at rs871911 in c11orf30,
    an A allele at rs59382353 in c11orf30,
    a G allele at rs73004436 in c11orf30,
    a G allele at rs4426156 in c11orf30,
    a C allele at rs61894509 in c11orf30,
    a G allele at rs61696910 in c11orf30,
    an A allele at rs61894530 in c11orf30,
    a T allele at rs11532107 in c11orf30,
    a G allele at rs142931944 in c11orf30,
    an A allele at rs11236766 in c11orf30,
    a T allele at rs61894534 in c11orf30,
    an A allele at rs11236767 in c11orf30,
    a C allele at rs57790584 in c11orf30,
    a T allele at rs7940373 in c11orf30,
    a G allele at rs61894541 in c11orf30,
    a G allele at rs1939469 in c11orf30,
    an A allele at rs11236775 in c11orf30,
    a T allele at rs61894547 in c11orf30,
    a T allele at rs3758716 in c11orf30,
    a T allele at rs3758715 in c11orf30,
    a C allele at rs17134961 in c11orf30,
    a T allele at rs2155221 in c11orf30, and
    an A allele at rs55646091 in c11orf30.

8. The method of claim 1, further comprising detecting at least one of an EoE associated SNP selected from a T allele at rs167769 in STAT6 and a T allele at rs73120411 in STAT6.

* * * * *